United States Patent
Yoshimura et al.

(10) Patent No.: US 9,631,176 B2
(45) Date of Patent: Apr. 25, 2017

(54) METHOD FOR PREPARING STEM CELLS FROM FAT TISSUE

(75) Inventors: Kotaro Yoshimura, Shibuya-ku (JP);
Daisuke Matsumoto, Taito-ku (JP)

(73) Assignee: BIOMASTER, INC., Chiyoda-Ku (JP)

( * ) Notice: Subject to any disclaimer, the term of this patent is extended or adjusted under 35 U.S.C. 154(b) by 1880 days.

(21) Appl. No.: 10/578,213

(22) PCT Filed: Nov. 4, 2004

(86) PCT No.: PCT/JP2004/016717
§ 371 (c)(1),
(2), (4) Date: Jan. 10, 2007

(87) PCT Pub. No.: WO2005/042730
PCT Pub. Date: May 12, 2005

(65) Prior Publication Data
US 2007/0148766 A1 Jun. 28, 2007

(30) Foreign Application Priority Data
Nov. 4, 2003 (JP) .................................. 2003-375026
Feb. 16, 2004 (JP) .................................. 2004-039099

(51) Int. Cl.
*C12N 5/00* (2006.01)
*C12N 5/0775* (2010.01)
*A61K 35/12* (2015.01)

(52) U.S. Cl.
CPC ............ *C12N 5/0667* (2013.01); *A61K 35/12* (2013.01)

(58) Field of Classification Search
CPC ........ A61K 35/28; A61K 35/35; A61K 35/12; C12N 5/0667; C12N 5/0662; C12N 5/0668; C12N 2509/00; C12M 47/04; C12M 45/05
See application file for complete search history.

(56) References Cited

U.S. PATENT DOCUMENTS 6,777,231 B1 * 8/2004 Katz et al. .................... 435/325
7,514,075 B2 * 4/2009 Hedrick et al. ............ 424/93.7

FOREIGN PATENT DOCUMENTS

| WO | 00/53795 A1 | 9/2000 |
|---|---|---|
| WO | 01/62901 A2 | 8/2001 |
| WO | 03/022988 A2 | 3/2003 |
| WO | 2005035738 | 4/2005 |

OTHER PUBLICATIONS

Gimble and Guilak, "Adipose-derived adult stem cells: isolation, characterization, and differentiation potential," *Cytotherapy* 5(5): 362-369, 2003.
Gronthos et al., "Integrin-mediated Interactions Between Human Bone Marrow Stromal Precursor Cells and the Extracellular Matrix," *Bone* 28(2): 174-181, Feb. 2001.
Gronthos et al., "Surface Protein Characterization of Human Adipose Tissue-Derived Stromal Cells," *J. of Cellular Physiology* 189: 54-63, Oct. 2001.
Mitchell et al., "Immunophenotype of Human Adipose-Derived Cells: Temporal Changes in Stromal-Associated and Stem Cell-Associated Markers," *Stem Cells* 24: 376-385, Feb. 2006.
Wagner and Ho, "Mesenchymal Stem Cell Preparations—Comparing Apples and Oranges," *Stem Cell Rev* 3: 239-248, Dec. 2007.
Zuk et al., "Multilineage Cells from Human Adipose Tissue: Implications for Cell-Based Therapies," *Tissue Engineering* 7(2): 211-228, Apr. 2001.
International Search Report dated Jul. 11, 2005 in Application No. PCT/JP2004/016717.
Written Opinion dated Jul. 7, 2005 in Application No. PCT/JP2004/016717.
International Preliminary Report on Patentability dated Jan. 13, 2006 in Application No. PCT/JP2004/016717.

* cited by examiner

*Primary Examiner* — Blaine Lankford
(74) *Attorney, Agent, or Firm* — Snell & Wilmer L.L.P.

(57) ABSTRACT

The present invention provides a method for preparing homogeneous stem cells and/or precursor cells in a large amount, in a simple and efficient manner, from human (in particular, the subject per se). The present invention further provides a method for preparing tissue implant or graft in a large amount by the use of the stem cells and/or precursor cells of the present invention. The present inventors have unexpectedly discovered that an aspirate from liposuction contains a large number of stem cells and have established a method for preparing stem cells from such an aspirate from liposuction, and thereby achieved the above-mentioned object.

21 Claims, 26 Drawing Sheets growth curve of stem cells prepared from material from liposuction without erythrocyte removal cultured on DMEM and M199.

Time lapse change of stem cells from stem cells from liposuction material without blood cells in DMEM medium.

| Day 6 | Day 8 |
|---|---|
| Day 10 | Day 12 | magnitude x10

Time lapse change of stem cells from stem cells from liposuction material without blood cells in DMEM medium.

Time lapse change of stem cells from stem cells from liposuction material without blood cells in M199 medium.

Time lapse change of stem cells from stem cells from liposuction material without blood cells in M199 medium.

METHOD FOR PREPARING STEM CELLS FROM FAT TISSUE

TECHNICAL FIELD

The present invention relates to a method or system for preparing stem cells from the aspirate from liposuction, and stem cells prepared by using such a method or system, as well as the use of the stem cells.

BACKGROUND ART

Regenerative medicine, mainly utilizing stem cells, has considerably progressed in recent years. Various tissue stem cells, which had not been considered to be present, were discovered and identified in various tissues. Thus, attention has been focused on disease therapy using regenerative therapy.

However, regenerative therapy has not yet reached a point where it is conventionally applied to numerous patients suffering from organ or tissue dysfunction. To date, a very limited number of such patients have been treated by organ transplantation or use of an auxiliary medical system or apparatus. These therapies are problematic in terms of shortage of donors, rejection, infection, durability, and the like. In particular, the donor shortage raises serious problems. In the case of bone marrow transplantation, bone marrow and umbilical cord blood banks have gradually become more widely used at home and abroad, though it is still difficult to provide a limited amount of samples to the number of patients in need. Therefore, there is an increasing demand for therapies using stem cells and regenerative medicine using the same in order to overcome the above-described problems. Use of foreign tissue for organ implantation (e.g., heart, blood vessels, etc.) is hindered mainly by immune rejection responses. Changes occurring in allogeneic grafts (or allografts) and xenografts are well known.

After gastrulation, a fertilized egg is divided into three germ layers, i.e., endoderm, mesoderm, and ectoderm. Cells derived from the ectoderm are mainly present in brain, including neural stem cells and the like. Cells derived from the mesoderm are mainly present in bone marrow, including blood vessel stem cells, hematopoietic stem cells, mesenchymal stem cells, and the like. Cells derived from the endoderm are mainly present in organs, including liver stem cells, pancreatic stem cells, and the like.

Mesenchymal cells, such as adipocytes, bone cells, ligament cells, cardiac muscle cells, and the like, have an important function of forming the shape or skeleton of the body. Therefore, there is an increasing expectation for the application of groups of such cells or tissues of such cells to regenerative medicine and implantation medicine. Particularly, it has been reported that bone marrow mesenchymal stem cells can be differentiated into mesodermal organs, and such stem cells have attracted attention mainly in the field of regenerative medicine. However, differentiation of such cells requires special conditions where a special medium containing a differentiation inducing agent (e.g., dexamethasone, etc) is required (Nakatsuji, ed., "Kansaibo•Kuron Kenkyu Purotokoru [Stem cell/Clone Research Protocol]", Yodosha (2001)).

Mesenchymal stem cells are a type of tissue stem cells. Mesenchymal stem cells naturally occur only in a small amount (one ten thousandth of all cells in the bone marrow of human neonates, thereafter reducing quickly, and one two millionth of all cells in elderly persons). It is therefore difficult to isolate mesenchymal stem cells. As it has been reported that mesenchymal stem cells are differentiated into germ layers other than mesoderm, the range of applications is becoming widespread. However, conditions for such differentiation are more specific than those which are described above. The known surface antigens of mesenchymal stem cells are CD105(+), CD73(+), CD29(+), CD44(+), CD14(−), CD34(−), and CD45(−).

Isolation of mesenchymal stem cells requires large costs. Further, taking bone marrow cells is generally associated with pain to the donor. Further, it is difficult to culture such cells without inducing differentiation serum from a specifically selected lot must be used thereby adding additional cost and labor to the use of such stem cells.

On the other hand, it has been found that fat contains stem cells (WO00/53795; WO03/022988; WO01/62901; Zuk, P. A., et al., Tissue Engineering, Vol. 7, 211-228, 2001; Zuk, P. A., et al., Molecular Biology of the Cell, Vol. 13, 4279-4295, 2002). A large amount of stem cells can be obtained from fat than other tissues (e.g., bone marrow, etc.) and the density of stem cells seem to be higher. Therefore, fat has attracted attention. Prior art methods for preparing stem cells from fat tissue (Japanese PCT National Phase Laid-Open Publication No. 2003-523267 and Japanese PCT National Phase Laid-Open Publication No. 2002-537849) have an advantage in availability in richer amount than when bone marrow is used as the cell source. However, it is necessary to treat the fat tissue, the cell source, with an enzyme such as collagenase, and therefore it is impossible to prepare stem cells in a simple and large amount. In considering application of stem cells and precursor cells to regenerative medicine, there is still demand for a method for preparing homogeneous stem cells and precursors in a simple manner and in a large amount.

SUMMARY OF INVENTION

It is an object of the present invention to provide a method for preparing homogeneous stem cells and/or precursor cells in a large amount, in a simple and efficient manner, from human (in particular, the subject per se).

It is another object of the present invention to provide a method for preparing tissue implant or graft in a large amount by the use of the stem cells and/or precursor cells of the present invention.

The present inventors have unexpectedly discovered that the aspirate from liposuction contains a large number of stem cells and have established a method for preparing stem cells from such an aspirate from liposuction, and thereby achieved the above-mentioned object.

Accordingly, the present invention provides the following:

1. A method for preparing a stem cell comprising:
   A) obtaining an aspirate from liposuction;
   B) subjecting the aspirate from liposuction to centrifugation to obtain a cell fraction
   C) subjecting the cell fraction to centrifugation by specific gravity; and
   D) collecting a cell layer with lower specific gravity than that of erythrocytes.
2. The method according to Item 1, wherein said aspirate from liposuction is prepared using saline or Ringer's solution.
3. The method according to Item 1, wherein said centrifugation is conducted at a speed of a range equal to or less than 800×g.

4. The method according to Item 1, wherein said centrifugation is conducted at a speed of a range equal to or less than 400×g.
5. The method according to Item 1, wherein said centrifugation by specific gravity is conducted at a speed of a range between 370×g and 1,100×g.
6. The method according to Item 1, wherein said centrifugation by specific gravity is conducted using medium which as a specific gravity of 1.076 to 1.078 g/ml at 20 degree Celsius.
7. The method according to Item 1, wherein the medium of said centrifugation by specific gravity is selected from the group consisting of Ficoll, Percoll and sucrose.
8. The method according to Item 7, wherein the medium of said centrifugation by specific gravity is Ficoll.
9. The method according to Item 1, wherein the specific gravity of the collected cell layer is at a range of between 1.050 and 1.075.
10. The method according to Item 1, wherein the collection of said cell layer is conducted using a pipette.
11. The method according to Item 1, further comprising the step of culturing said cell layer in a medium containing components selected from the group consisting of DMEM, M199, MEM, HBSS, Ham's F12, BME, RPMI1640, MCDB104, MCDB153 (KGM) and a mixture thereof.
12. The method according to Item 1, wherein the centrifugation by specific gravity comprises density gradient centrifugation.
13. The method according to Item 1, further comprising the step of removing blood cells.
14. A method for preparing a stem cell comprising:
  A) obtaining material from liposuction; and
  B) subjecting the material from liposuction to centrifugation to obtain a cell fraction without isolation of fat tissue.
15. The method according to Item 14, further comprising the step of subjecting the material to a condition where at least a portion of cells are separated from the material.
16. The method according to Item 15, wherein the condition is for degradation of extracellular matrices.
17. The method according to Item 15, said degradation of extracellular matrices is achieved by a collagenase.
18. The method according to Item 14, further comprising the step of removing supernatant in step B).
19. The method according to Item 14, further comprising the step of filtering the material from the step B).
20. The method according to Item 14, further comprising the step of removing blood cells.
21. The method according to Item 14 wherein the step of removing blood cells comprises adding a component of degrading blood cells.
22. A method for preparing a stem cell comprising:
  i) obtaining material from liposuction;
  ii) subjecting the material to a condition where at least a portion of cells are separated from the material, without isolation of fat tissue;
  iii) subjecting the material to centrifugation;
  iv) adding a component degrading blood cells to the material and agitating the material;
  v) subjecting the material to centrifugation to obtain a pellet; and
  vi) aspirating supernatant of the material from the pellet.
23. The method according to Item 22, wherein the step of subjecting the material to said condition comprises maintaining an aspirate from the liposuction.
24. The method according to Item 22, wherein said material from liposuction comprises an aspirate from liposuction and fat.
25. The method according to Item 22, wherein said condition in said step ii) comprises adding a collagenase.
26. The method according to Item 22, wherein the centrifugation in said step iii) is conducted at 400-1200×g.
27. The method according to Item 22, wherein said component degrading blood cells comprises ammonium chloride and potassium bicarbonate.
28. The method according to Item 27, wherein said ammonium chloride is comprised in the component at 155 mM
29. The method according to Item 27, wherein said potassium bicarbonate is comprised in the component at 10 mM.
30. The method according to Item 22, wherein said centrifugation in said step v) is conducted at 400-1200×g.
31. The method according to Item 22, wherein said pellet contains a stem cell.
32. A stem cell prepared by the method according to any of Items 1-31.
33. The stem cell according to Item 32, which expresses at least one protein selected from the group consisting of CD13, CD29, CD34, CD36, CD44, CD49d, CD54, CD58, CD71, CD73, CD90, CD105, CD106, CD151 and SH3.
34. The stem cell according to Item 33, which expresses CD13, CD29, CD34, CD36, CD44, CD49d, CD54, CD58, CD71, CD73, CD90, CD105, CD106, CD151 and SH3.
35. The stem cell according to Item 33, further expressing at least one protein selected from the group consisting of CD31, CD45, CD117 and CD146.
36. The stem cell according to Item 32, which does not express CD56.
37. The stem cell according to Item 32, which does not express at least one protein selected from the group consisting of CD3, CD4, CD14, CD15, CD16, CD19, CD33, CD38, CD56, CD61, CD62e, CD62p, CD69, CD104, CD135 and CD144.
38. The stem cell according to Item 37, which does not express CD3, CD4, CD14, CD15, CD16, CD19, CD33, CD38, CD56, CD61, CD62e, CD62p, CD69, CD104, CD135 and CD144.
39. The stem cell according to Item 32, which expresses CD49d and does not express CD56.
40. A system for preparing a stem cell comprising:
  A) means for obtaining an aspirate from liposuction;
  B) means for subjecting the aspirate from liposuction to centrifugation to obtain a cell fraction; and
  C) means for subjecting the cell fraction to centrifugation by specific gravity.
41. The system according to Item 40, wherein the system further comprises:
  D) means for collecting a cell layer with lower specific gravity than that of erythrocytes.
42. A system for preparing a stem cell comprising:
  A) means for obtaining material from liposuction; and
  B) means for subjecting the material from liposuction to centrifugation to obtain a cell fraction without isolation of fat tissue.
43. A system for preparing a stem cell comprising:
  i) means for obtaining material from liposuction;
  ii) means for subjecting the material to a condition where at least a portion of cells are separated from the material, without isolation of fat tissue;
  iii) means for subjecting the material to centrifugation;
  iv) a component degrading blood cells to the material and agitating the material;
  v) means for subjecting the material to centrifugation to obtain a pellet; and
  vi) means for aspirating supernatant of the material from the pellet.

44. A method for obtaining an explant comprising:
  A) obtaining an aspirate from liposuction;
  B) subjecting the aspirate from liposuction to centrifugation to obtain a cell fraction;
  C) subjecting the cell fraction to centrifugation by specific gravity;
  D) collecting a cell layer with lower specific gravity than that of erythrocytes;
  E) culturing the collected cell layer to obtain an explant.

45. A method for preparing a tissue transplant comprising:
  A) obtaining an aspirate from liposuction;
  B) subjecting the aspirate from liposuction to centrifugation to obtain a cell fraction; and
  C) culturing the collected cell layer to obtain a tissue transplant.

46. A method for preparing tissue transplant comprising:
  A) obtaining an aspirate from liposuction;
  B) subjecting the aspirate from liposuction to centrifugation to obtain a cell fraction;
  C) subjecting the cell fraction to centrifugation by specific gravity;
  D) collecting a cell layer with lower specific gravity than that of erythrocytes;
  E) culturing the collected cell layer to obtain a tissue transplant.

47. A method for transplanting a tissue transplant comprising:
  A) obtaining an aspirate from liposuction;
  B) subjecting the aspirate from liposuction to centrifugation to obtain a cell fraction;
  C) subjecting the cell fraction to centrifugation by specific gravity;
  D) collecting a cell layer with lower specific gravity than that of erythrocytes;
  E) culturing the collected cell layer to obtain a tissue transplant; and
  F) transplanting the tissue transplant.

48. Use of an aspirate of liposuction in preparing stem cells.

49. A method for preparing cells selected from the group consisting vascular endothelial precursor cells, adipocytes, cartilage cells, bone cells and muscle cells comprising the step of culturing a stem cell obtained by the method according to any one of Items 1-31.

50. A method for preparing a differentiated cell comprising:
  A) obtaining a mixture by mixing
    a) the stem cell obtained according to any one of Items 1-31, and
    b) a differentiated cell corresponding to a desired site; and
  B) culturing the mixture under sufficient conditions which allow the adipose-derived precursor cell to differentiate.

51. The method according to item 50, wherein the differentiated cell is a mesenchymal cell.

52. The method according to item 50, wherein the differentiated cell is selected from the group consisting of adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, renal cells, and pancreas cells.

53. The method according to item 50, further comprising providing an agent for promoting differentiation into said differentiated cell.

54. The method according to item 50, wherein the mixture is cultured in a medium containing at least one ingredient selected from the group consisting of adrenocortical steroids, insulin, glucose, indomethacin, isobutyl-methylxanthine (IBMX), ascorbic acid and a derivative thereof, glycerophosphate, estrogen and a derivative thereof, progesterone and a derivative thereof, androgen and a derivative thereof, growth factors, pituitary gland extracts, pineal body extracts, retinoic acid, vitamin D, thyroid hormone, fetal bovine serum, equine serum, human serum, heparin, sodium hydrogen carbonate, HEPES, albumin, transferring selenates, linoleic acid, 3-isobutyl-1-methylxanthine demethylating agent, histone deacetylating agents, activin, cytokine, hexamethylenebisacetamide (HMBA), dimethylacetamide (DMA), dibutyl cAMP (dbcAMP), dimethylsulfoxide (DMSO), iododeoxyuridine (IdU), hyroxyurea (HU), cytosine arabinoside (AraC), mitomycin C (MMC), sodium butyrate (NaBu), polybrene, and selenium.

55. A cell mixture, comprising a stem cell obtained according to any one of Items 1-31; and a differentiated cell corresponding to a desired site.

56. The cell mixture according to Item 55, wherein the cell mixture is subjected to conditions sufficient for inducing the differentiation of the stem cell.

57. A composition for cell transplantation comprising:
  a) a stem cell obtained according to any one of Items 1-31; and
  b) a differentiated cell corresponding to a desired site.

58. The composition according to Item 57, wherein the transplantation is conducted at the desired site.

59. The composition according to Item 57, wherein the ratio between the stem cell and the differentiated cell is about 1:10 to about 10:1.

60. The composition according to Item 57, wherein the ratio between the stem cell and the differentiated cell is about 1:2 to about 2:1.

61. The composition according to Item 57, wherein the ratio between the stem cell and the differentiated cell is substantially the same.

62. The composition according to Item 57, wherein said differentiated cell comprises a mesenchymal cell.

63. The composition according to Item 57, wherein the differentiated cell is selected from the group consisting of adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, renal cells, and pancreas cells.

64. The composition according to Item 57, further comprising at least one ingredient selected from the group consisting of adrenocortical steroids, insulin, glucose, indomethacin, isobutyl-methylxanthine (IBMX), ascorbic acid and a derivative thereof, glycerophosphate, estrogen and a derivative thereof, progesterone and a derivative thereof, androgen and a derivative thereof, growth factors, pituitary gland extracts, pineal body extracts, retinoic acid, vitamin D, thyroid hormone, fetal bovine serum, equine serum, human serum, heparin, sodium hydrogen carbonate, HEPES, albumin, transferrin, selenates, linoleic acid, 3-isobutyl-1-methylxanthine, demethylating agent, histone deacetylating agents, activin, cytokine, hexamethylenebisacetamide (HMBA), dimethylacetamide (DMA), dibutyl cAMP (dbcAMP), dimethylsulfoxide (DMSO), iododeoxyuridine (IdU), hyroxyurea (HU), cytosine arabinoside (AraC), mitomycin C (MMC), sodium butyrate (NaBu), polybrene, and selenium.

65. The composition according to Item 57, wherein the stem cell and the differentiated cell are allogeneic to each other.

66. The composition according to Item 57, wherein the stem cell and the differentiated cell are syngeneic to each other.

67. A method for treating or preventing a disease, disorder or an abnormal condition associated with a failure of a differentiated cell, comprising:
  A) providing a composition comprising:
  a) a stem cell obtained according to any one of Items 1-31; and
  b) a differentiated cell corresponding to a desired site; and
  B) administering the composition to a subject.
68. A medicament for treatment or prevention of a disease, a disorder or an abnormal condition attributed to the deficiency of a differentiated cell, comprising:
  a) a stem cell obtained according to any one of Items 1-31;
  b) a differentiated cell corresponding to a desired site; and
  c) a pharmaceutically acceptable carrier.
69. Use of a mixture of: a) a stem cell obtained according to any one of Items 1-31; and b) a differentiated cell corresponding to a desired site, for preparation of a medicament for treatment or prevention of a disease, a disorder or an abnormal condition attributed to the deficiency of a differentiated cell.
70. A method for treatment or improvement of a cosmetic condition, comprising the steps of:
  A) providing a composition comprising:
  a) a stem cell obtained according to any one of Items 1-26; and
  b) a differentiated cell corresponding to a desired site; and
  B) administering the composition to a subject.
71. A medicament for treatment or improvement of a cosmetic condition, comprising:
  a) a stem cell obtained according to any one of Items 1-31;
  b) a differentiated cell corresponding to a desired site; and
  c) a pharmaceutically acceptable carrier.
72. Use of a mixture of: a) a stem cell obtained according to any one of Items 1-31; and b) a differentiated cell corresponding to a desired site, for preparation of a medicament for treatment or improvement of a cosmetic condition.

Effects of the Invention

The present invention provides a method for preparing homogeneous stem cells and/or precursor cells in a large amount, in a simple and efficient manner, from human (in particular, the subject per se).

The present invention further provides a method for preparing a tissue implant or graft in a large amount by the use of the stem cells and/or precursor cells of the present invention.

The present invention further provides stem cells, precursor cells, tissues, organs prepared using the cells.

The present invention provides novel methods for preparing stem cells from fat, in a simple and efficient manner than the conventional methods. The present methods achieved significant effects of providing large volume/amount of stem cells by making use of an aspirate from fat tissue.

Hereinafter, the present invention will be described by way of preferable examples. It will be understood by those skilled in the art that the examples of the present invention can be appropriately made or carried out based on the description of the present specification and commonly used techniques well known in the art. The function and effect of the present invention can be easily recognized by those skilled in the art.

BRIEF DESCRIPTION OF THE DRAWINGS

FIG. 8=Round 2; Days 3, 5, 7 and 9) and M199 medium (FIG. 9=Round 1; Days 6, 8, 10 and 12; and FIG. 10=Round 2; Days 3, 5, 7 and 9).

TABLE

Figure legends

Figure 1:
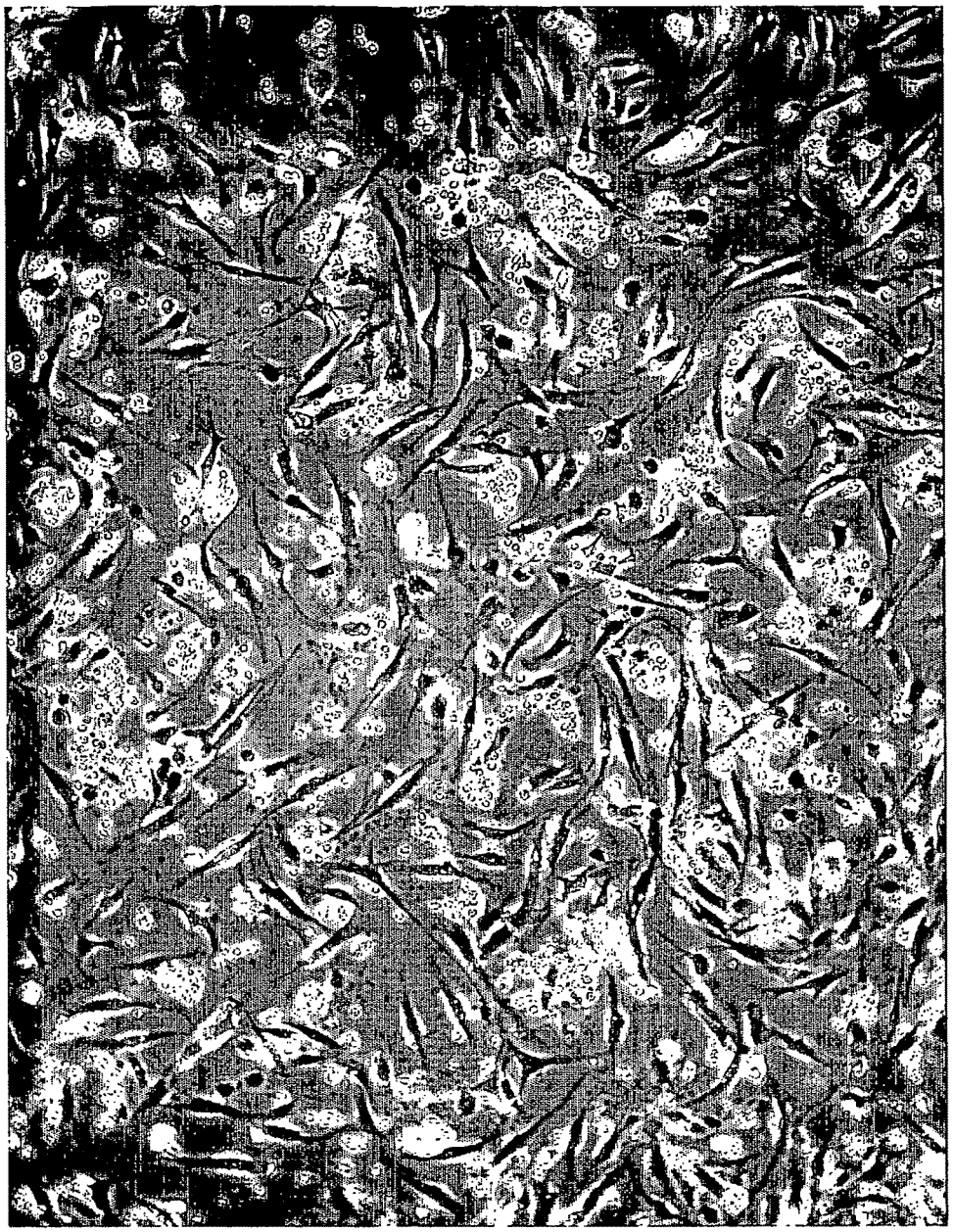
FIG. 1 is a photograph showing stem cells derived from a liquid portion of an aspirate from liposuction, which was prepared according to the present invention.

| FIG. No. | days of culture (induction) | culture medium | magnitude | culture/ seed | control/ induction |
|---|---|---|---|---|---|
| 11 | 12 days | adipocyte differentiation | x10 | culture | induction |
| 12 | 12 days | adipocyte differentiation | x20 | culture | induction |
| 13 | 12 days | adipocyte differentiation | x10 | culture | control |
| 14 | 12 days | adipocyte differentiation | x20 | culture | control |
| 15 | 33 days | chondrocyte differentiation | x10 | culture | induction |
| 16 | 35 days | chondrocyte differentiation | x10 | culture | induction |
| 17 | 33 days | chondrocyte differentiation | x10 | culture | control |
| 18 | 35 days | chondrocyte differentiation | x10 | culture | control |
| 19 | 22 days | osteocyte differentiation | x10 | culture | induction |
| 20 | 22 days | osteocyte differentiation | x10 | culture | control |
| 21 | 25 days | adipocyte differentiation | x20 | seed | induction |
| 22 | 25 days | adipocyte differentiation | x10 | seed | induction |
| 23 | 25 days | adipocyte differentiation | x20 | seed | control |
| 24 | 25 days | adipocyte differentiation | x10 | seed | control |

TABLE-continued

Figure legends

| FIG. No. | days of culture (induction) | culture medium | magnitude | culture/ seed | control/ induction |
|---|---|---|---|---|---|
| 25 | 22 days | osteocyte differentiation | x10 | seed | induction |
| 26 | 22 days | osteocyte differentiation | x10 | seed | control |

Cells prepared according to the present invention were seeded on to a 60-mm dish at the density of $1.8 \times 10^7$ cells/dish. Induction was conducted in two groups. For one group, after culturing for ten days, each differentiation induction medium. (adipocyte differentiation, chondrocyte differentiation and osteocyte differentiation media) was replaced with the original medium (herein also called "culture"). For the other group, no culture was conducted before the induction started (herein also called "seed". Evaluation after induction was conducted using Oil-Red O for adipocytes, Alcian blue for chondrocytes, and von Kossa staining for osteocytes.

These and other advantages of the present invention will be apparent from the drawings and a reading of the detailed description thereof.

BEST MODE FOR CARRYING OUT THE INVENTION

Hereinafter, the present invention will be described. It should be understood throughout the present specification that articles for singular forms (e.g., "a", "an", "the", etc. in English) include plural referents unless the context clearly dictates otherwise. It should be also understood that the terms as used herein have definitions typically used in the art unless otherwise mentioned. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. It should be also understood that terms as used herein have definitions ordinarily used in the art unless otherwise mentioned. Therefore, all technical and scientific terms used herein have the same meanings as commonly understood by those skilled in the art. Otherwise, the present application (including definitions) takes precedence.

DEFINITION OF TERMS

Terms particularly used herein are defined as follows.

The term "cell" is herein used in its broadest sense in the art, referring to a structural unit of tissue of a multicellular organism, which is capable of self replicating, has genetic information and a mechanism for expressing it, and is surrounded by a membrane structure which isolates the living body such as a cell from the outside. In the method of the present invention, any cell can be used as a subject. The number of cells used in the present invention can be counted through an optical microscope. When counting using an optical microscope, the number of nuclei is counted. Tissues are sliced into tissue sections, which are then stained with hematoxylin-eosin (HE) to distinguish nuclei derived from extracellular matrices (e.g., elastin or collagen) and cells. These tissue sections are observed under an optical microscope and the number of nuclei in a particular area (e.g., 200 µm×200 µm) can be estimated to be the number of cells. Cells used herein may be either naturally-occurring cells or artificially modified cells (e.g., fusion cells, genetically modified cells, etc.). Examples of cell sources include, but are not limited to, a single-cell culture; the embryo, blood, or somatic tissue (e.g., adipose or fat tissue) of a normally-grown transgenic animal; a cell mixture of cells derived from normally-grown cell lines; and the like. Such a supply source itself can be used as cells.

Fat cells (adipocytes) and their corresponding material used in the present invention may be derived from any organism (e.g., Myxiniformes, Petronyzoniformes, Chondrichthyes, Osteichthyes, Amphibia, Reptilia, Aves, Mammalia, etc.), more preferably mammalian (e.g., Monotremata, Marsupialia, Edentate, Dermoptera, Chiroptera, Carnivora, Insectivora, Proboscidea, Perissodactyla, Artiodactyla, Tubulidentata, Pholidota, Sirenia, Cetacean, Primates, Rodentia, Lagomorpha, etc.) as long as such an organism has adipocytes or cells corresponding thereto. In one embodiment, cells derived from Primates (e.g., chimpanzee, Japanese monkey, human) are used. Most preferably, cells derived from a human are used, but the present invention is not limited thereto.

As used herein, the term "stem cell" refers to a precursor (or progenitor) of a differentiated cell, which has monopotency, multipotency, or totipotency. Stem cells can be differentiated in response to specific stimuli. Typically, stem cells can regenerate an injured tissue. Stem cells used herein may be, but are not limited to, embryonic stem (ES) cells, tissue stem cells (also called tissular stem cell, tissue-specific stem cell, or somatic stem cell), or other precursor cells. A stem cell may be an artificially produced cell (e.g., fusion cells, reprogrammed cells, or the like used herein) as long as it can have the above-described abilities. Embryonic stem cells are pluripotent stem cells derived from early embryos. An embryonic stem cell was first established in 1981, which has been applied to production of knockout mice since 1989. In 1998, a human embryonic stem cell was established, which is currently becoming available for regenerative medicine. Tissue stem cells have a relatively limited level of differentiation unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, a long cell cycle, and proliferative ability beyond the life of the individual. As used herein, stem cells may be preferably embryonic stem cells, though tissue stem cells may also be employed depending on the circumstance.

Tissue stem cells are separated into categories based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, "precursor cell" refers to a cell which corresponds to an undifferentiated parent cell having no differentiation property, when the progeny cell thereof is known to have a specific differentiation property, and includes not only multipotent undifferentiated cells but also monopotent undifferentiated cells. For example, when a progeny cell is a vascular endothelial cell, then the precursor cell thereof is a vascular endothelial precursor cell. As used herein, the term "stem cell" encompasses precursor cells. However, it can be said that a precursor cell obtained by differentation of a stem cell, corresponds to "differentiated cell" in terms of the stem cell. The term "PLA (processed lipoaspirate cell)" refers to a precursor cell which is obtained from the fat proportion (lipoaspirate) of an aspirate from liposuction. Precursor cells derived from a liquid portion of an aspirate from liposuction may be referred to as "liquid-aspirate cells" or "LAF". Adipose-derived precursor cells include PLA cells and liquid-aspirate cells.

As used herein, the term "adipose-derived precursor cell" refers to a stem cell and also other precursor cells, such as stem cells from peripheral blood or vascular-stromal cells (preadipocytes), obtained from liposuction. Adipose-derived precursor cells mean any multipotent or monopotent precursor cell populations derived from the adipose tissue or obtained from liposuction procedure. The cells include adipose-derived vascular-stromal cells (=preadipocytes, adipose-derived interstitial cells), adipose-derived stem cells, fat stem cells, endothelial progenitor cells, hematopoietic stem cells, and so on. Some techniques for isolating such a stem cell are known as described in, for example, Nakatsuji, ed., "Kansaibo•Kuron Kenkyu Purotokoru [Stem cell/Clone. Research Protocol]", Yodosha (2001); WO00/53795; WO03/022988; and WO01/62901. These documents are herein incorporated by reference in their relevant portions. As used herein, the term "adipose-derived precursor cell" refers to all fat tissue-derived stem cells including fat tissue-derived stem cells obtained by these known isolation methods. As used herein, the term "precursor cell" includes not only multipotent undifferentiated cells but also monopotent undifferentiated cells. As used herein, the term "stem cell" encompasses precursor cells. The term "PLA (processed lipoaspirate cell)" refers to a precursor cell which is obtained from the fat proportion (lipoaspirate) of an aspirate from liposuction. Precursor cells derived from a liquid portion of an aspirate from liposuction may be referred to as "liquid-aspirate cells". Adipose-derived precursor cells include PLA cells and liquid-aspirate cells.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as long as the cells can achieve the intended treatment.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, adipocytes, bone cells, chondrocytes, and the like. Differentiated cells used in the present invention may be in the form of a group or tissue.

The origin of a cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells and differentiated cells thereof, hematopoietic stem cells and differentiated cells thereof, mesenchymal stem cells and differentiated cells thereof, and the like. Stem cells of mesoderm origin are mostly present in organs, including liver stem cells and differentiated cells thereof, pancreatic stem cells and differentiated cells thereof, and the like. Somatic cells may be herein derived from any germ layer. Preferably, mesenchymal somatic cells may be used.

As used herein, the term "mesenchymal stem cell" refers to a stem cell found in mesenchyme. The term "mesenchymal stem cell" may be herein abbreviated as "MSC". Mesenchyme refers to a population of free cells which are in an asterodal shape or have irregular projections and bridge gaps between epithelial tissues, and which are recognized in each stage of development of multicellular animals. Mesenchyme also refers to tissue formed with intracellular cement associated with the cells. Mesenchymal stem cells have proliferative ability and the ability to differentiate into bone cells, chondrocytes, muscle cells, stroma cells, tendon cells, and adipocytes. Mesenchymal stem cells are employed in order to culture or grow bone marrow cells or the like collected from patients, or differentiate them into chondrocytes or osteoblasts. Mesenchymal stem cells are also employed as reconstructive material, such as alveolar bones; bones, cartilages or joints for arthropathy or the like; and the like. There is a large demand for mesenchymal stem cells. Also, mesenchymal stem cells can be differentiated into blood cells and lymphoid cells. Therefore, there is an increasing demand for mesenchymal stem cells.

The phrase "material from liposuction" refers to any material generated when liposuction is conducted. Typically such material from liposuction contains fat tissue and an aspirate from liposuction.

The phrase "an aspirate from liposuction" refers to a liquid generated when liposuction is conducted. Such an aspirate from liposuction may be but not limited to: (1) a liquid aspirated when liposuction is conducted (for example, including Tumecent solution and blood) or (2) a liquid caused by washing aspirated fat with a solution such as saline.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as long as they can achieve the intended treatment.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, adipocytes, bone cells, chondrocytes, and the like. Differentiated cells used in the present invention may be in the form of a group of cells or a tissue.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells and differentiated cells thereof, hematopoietic stem cells and differentiated cells thereof, mesenchymal stem cells and differentiated cells thereof, and the like. Stem cells of mesoderm origin are mostly present in organs, including liver stem cells and differentiated cells thereof, pancreatic stem cells and differentiated cells thereof, and the like. Somatic cells may be herein derived from any germ layer. Preferably, mesenchymal somatic cells may be used.

As used herein, the term "adipocyte" refers to a cell which is located between tissues or forms fat tissue as areolar tissue or a group along capillary blood vessels, and which contains a large amount of lipid. Fat cells include a yellow adipocyte and a brown adipocyte. These cells may be equivalently used herein. Fat within cells can be easily detected with Sudan III or osmium tetroxide.

As used herein, the term "desired site" refers to any portion of a subject for which treatment is desired. In the present invention, it will be understood that such a desired site may be selected from any organ or tissue of a subject.

As used herein, the term "tissue" refers to an aggregate of cells having substantially the same function and/or form in a multicellular organism. "Tissue" is typically an aggregate of cells of the same origin, but may be an aggregate of cells of different origins as long as the cells have the same function and/or form. Therefore, when stem cells of the present invention are used to regenerate tissue, the tissue may be composed of an aggregate of cells of two or more different origins. Typically, a tissue constitutes a part of an organ. Animal tissues are separated into epithelial tissue, connective tissue, muscular tissue, nervous tissue, and the like, on a morphological, functional, or developmental basis. Plant tissues are roughly separated into meristematic tissue and permanent tissue according to the development stage of the cells constituting the tissue. Alternatively, tissues may be separated into single tissues and composite tissues according to the type of cells constituting the tissue. Thus, tissues are separated into various categories. Any tissue may be herein intended as a target to be treated.

Any organ may be targeted by the present invention. A tissue or cell targeted by the present invention may be derived from any organ. As used herein, the term "organ" refers to a morphologically independent structure localized at a particular portion of an individual organism in which a certain function is performed. In multicellular organisms (e.g., animals, plants), an organ consists of several tissues spatially arranged in a particular manner, each tissue being composed of a number of cells. An example of such an organ includes an organ relating to the vascular system. In one embodiment, organs targeted by the present invention include, but are not limited to, skin, blood vessel, cornea, kidney, heart, liver, umbilical cord, intestine, nerve, lung, placenta, pancreas, brain, peripheral limbs, retina, and the like. Any organ may be herein used as a target. Preferably, mesenchymal tissue (e.g., fat, bone, ligament, etc.) may be targeted, without limitation.

As used herein, the term "conditions sufficient for differentiation" refers to time, medium, temperature, humidity, and the like which cause differentiation. A method for preparing a differentiated cell from a stem cell derived from an aspirate from liposuction includes (1) a method for adding a differentiation inducer into a medium; and (2) a method for culturing the cell of the present invention with a differentiated cell corresponding to the site of desire.

A method for adding a differentiation inducer (for example, dexamethasone) into a medium, includes a method for adding to a culture medium of a stem cell, a conventionally known differentiation inducer (such as adrenocortical steroids such as dexamethasone, insulin, glucose, indomethacin, isobutyl-methylxanthine (IBMX), ascorbate-2-phosphate, ascorbic acid and a derivative thereof, glycerophosphate, estrogen and a derivative thereof, progesterone and a derivative thereof, androgen and a derivative thereof, growth factors such as αFGF, βFGF, EGF, IGF, TGF-beta, ECGF, BMP, PDGF, pituitary gland extracts, pineal body extracts, retinoic acid, vitamin D, thyroid hormone, fetal bovine serum, equine serum, human serum, heparin, sodium hydrogen carbonate, HEPES, albumin, transferrin, selenates (such as sodium selenite), linoleic acid, 3-isobutyl-1-methylxanthine, demethylating agent such as 5-azacytidine, histone deacetylating agents such as trichostatin, activin, cytokines such as LIF, IL-2, IL-6, hexamethylenebisacetamide (HMBA), dimethylacetamide (DMA), dibutyl cAMP (dbcAMP), dimethylsulfoxide (DMSO), iododeoxyuridine (IdU), hyroxyurea (HU), cytosine arabinoside (AraC), mitomycin C (MMC), sodium butyrate (NaBu), polybrene, and selenium.

In the method (2) for culturing a stem cell with a differentiated cell corresponding to a desired site, in accordance with the disclosure herein, by blending an adipose-derived precursor cell with a differentiated cell, the adipose-derived precursor cell is destined to become the differentiated cell. According to the present specification, it will be understood that such conditions overlap with conditions for maintaining adipose-derived precursor cells or differentiated cells singly. Therefore, the conditions may be changed as appropriate. Preferably, the conditions may be changed depending on the adipose-derived precursor cell of the present invention and a differentiated cell to be combined therewith and the composition of the mixture thereof. Once such preferable conditions are established, the conditions may be subsequently used for treatment of similar mixtures. In the present invention, such conditions for differentiation may be used for either in vitro, in vivo, or ex vivo situations. In the in vivo case, conditions which are provided within the implanted site of the body are used as they are. In the present invention, immediately after a stem cell and a differentiated cell are mixed, the mixture may be implanted into an in vivo environment or may be co-cultured in vitro. Autologous transplantation may be called ex vivo transplantation.

As used herein, the term "in vivo" refers to within an organism(s). In a specific context, "in vivo" refers to a position at which a subject tissue or organ is placed (e.g., a desire site as used herein).

As used herein, "in vitro" indicates that a part of an organism is extracted or released outside the organism for various purposes of research (e.g., in a test tube). The term in vitro is in contrast to the term in vivo.

As used herein, the term "ex vivo" refers to a series of operations where target cells into which a gene will be introduced are extracted from a subject; a therapeutic gene is introduced in vitro into the cells; and the cells are returned into the same subject.

An example of conditions for differentiation can be independently selected from the following: culture for 5 hours or more, pH of 5 to 10, temperature of 20° C. to 45° C. (e.g., 37° C.), humidity of 80% or more (e.g., 100%), use of M199 medium, supplement of 5 mg/500 ml heparin, supplement of 2 µg/500 ml acidic FGF, supplement of FBS (15%), supplement of $NaHCO_3$, oxygen concentration of 10 to 30% (e.g., 20%), $CO_2$ concentration of 2 to 10% (e.g., 5%), use of a gelatin coated dish, the presence of feeder cells, and the like. As an example, conditions are: culture for 5 hours, M199 medium (500 ml supplemented with 2.2 g of $NaHCO_3$, FBS (15%), 2 µg of acidic FGF, and 5 mg of heparin), at 37° C., 20% oxygen, 5% carbonic acid gas, 100% humidity, and culture in a gelatin coated dish. The present invention is not limited to this.

The above-described conditions may be used for the maintenance of differentiated cells (e.g., adipocytes) and adipose-derived precursor cells. The present invention is not limited to this.

For the differentiation of adipose-derived precursor cells, any culture medium containing an agent for promoting differentiation of the cells may be used for culture. Such a medium may be, for example, without limitation, DMEM supplemented with 10% FBS, 0.5 mM isobutylmethyl xanthine (IBMX), 1 μM dexamethasone, 10 μM insulin, and 200 μM indomethacin. The medium may be used at 37° C., 20% oxygen, 5% carbonic acid gas, and 100% humidity.

As used herein, the term "agent promoting the differentiation into a differentiated cell" or "differentiation promoting agent" refers to any agent which is known to promote differentiation into a differentiated cell (e.g., a chemical substance, temperature, etc.). Examples of such an agent include, but are not limited to, various environmental agents, such as temperature, humidity, pH, salt concentration, nutrients, metals, gas, organic solvents, pressure, chemical substances (e.g., steroids, antibiotics, etc.), and the like, or any combination thereof. Representative examples of such an agent include, but are not limited to, DNA demethylating agents (e.g., 5-azacytidine, etc.), histone deacetylating agents (e.g., trichostatin, etc.), intranuclear receptor ligands (e.g., retinoic acids (ATRA), vitamin D3, T3, etc.), cell growth factors (activin, IGF-1, FGF, PDGF, TGF-β, BMP2/4, etc.), cytokines (e.g., LIF, IL-2, IL-6, etc.), hexamethylenebisacetamide, dimethylacetamide, dibutyl cAMP, dimethylsulfoxide, iododeoxyuridine, hydoxyl urea, cytosine arabinoside, mitomycin C, sodium butyrate, aphidicholine, fluorodeoxyuridine, polybrene, selenium, etc. However, differentiated cells were not conventionally considered to be used as differentiation promoting agents. This is because differentiated cells release agents which suppress differentiation.

As used herein, the term "corresponding to a desired site" in relation to a cell, a tissue, an organ, or the like, which is intended to be used for implantation or regeneration according to the present invention, indicates that the cell or the like was obtained from the desired site (e.g., a heart-derived cell, etc.) or the cell or the like has substantially the same properties as those of a cell present at the desired site (e.g., a cell differentiated into a heart cell, etc.). Therefore, a cell can be confirmed to correspond to a desired site if the cell has substantially the same feature (e.g., a cell surface marker, etc.) as that of a cell at a desired site.

Examples of markers useful for the determination of a cell corresponding to such a desired site include, but are not limited to, (1) fat: the presence of triglycerides within the cytoplasm, OilRed-O staining, glycerophosphatedehydrogenase (Glycerophosphate dehydrogenase=GPDH) activity, GLUT4 within the cytoplasm, Ap2 (fatty acid binding protein), LPL (lipoprotein lipase), PPARγ1,2 (peroxisome growth activating receptor γ1,2), and the expression of leptin; (2) bone cell, bone tissue: the presence of alkaliphosphatase, the confirmation of the degree of bone calcification (precipitation of calcium), and the expression of osteocalcin, osteopontin, or osteonectin; (3) chondrocyte, cartilage tissue: the presence of mucopolysaccharides, the expression/presence of type II collagen, chondroitin-4-sulfate; (4) skeletal muscle cells: the presence of abundant myosin within the cytoplasm; and the like.

As used herein, the term "implantation" and "transplantation", which are interchangeably used herein, refers to an insertion of the cell, composition, medicament, or the like of the present invention into the body singly or in combination with other therapeutic agents. In the present invention, the following method, form, and amount may be used for introduction into a therapy site (e.g., bone, etc.): the medicament of the present invention is directly injected into, adhered and stitched to, inserted into, or the like, an injured site. A combination of an adipose-derived precursor cell and a differentiated cell of the present invention may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously (e.g., a differentiation promoting agent, etc.). Administration "in combination" further includes the separate administration of one of the compounds or agents given first, followed by the second.

As used herein, the term "autologous" or "self" in relation to an entity refers to the whole or a part (e.g., a cell, a tissue, an organ, etc.) of the same entity. As used herein, the term "autologous" or "self" may encompass a graft from a genetically identical individual (e.g. an identical twin) in a broad sense.

As used herein, the term "allogenic" refers to the whole or a part (e.g., a cell, a tissue, an organ, etc.) of an entity which is implanted from another entity which is the same species but is genetically different. Since an allogenic entity is genetically different, the allogenic entity may elicit an immune reaction in an entity (recipient) to which the allo-entity is implanted. Such a cell includes, for example, without limitation, a cell derived from its parent.

As used herein, the term "heterologous" refers to a material such as a cell or tissue which is implanted from a different species entity. Therefore, for example, when a human is a recipient, a porcine-derived graft is called a heterologous graft.

As used herein, a "recipient" (acceptor) refers to an entity which receives an implanted cell or the like and is also called "host". In contrast, an entity providing an implanted cell or the like is called a "donor" (provider). A donor may be the same as or different from a recipient.

A cell used in the present invention may be derived from an autologous origin (syngeneic origin), an allogenic origin (non-self origin), or a heterologous origin. In view of rejection reactions, syngeneic cells are preferable. If rejection reactions do not raise problems, allogenic cells may be employed.

As used herein, the term "disease, disorder, or abnormal condition attributed to the deficiency of a differentiated cell" refers to any disease, disorder, or abnormal condition in which the differentiated cell is involved. Such a differentiated cell may be preferably, without limitation, a mesenchymal cell.

In one embodiment, diseases and disorders targeted by the present invention may be of the circulatory system (blood cells, etc.). Examples of the diseases or disorders include, but are not limited to, anemia (e.g., aplastic anemia (particularly, severe aplastic anemia), renal anemia, cancerous anemia, secondary anemia, refractory anemia, etc.), cancer or tumors (e.g., leukemia); and after chemotherapy therefor, hematopoietic failure, thrombocytopenia, acute myelocytic leukemia (particularly, a first remission (high-risk group), a second remission and thereafter), acute lymphocytic leukemia (particularly, a first remission, a second remission and thereafter), chronic myelocytic leukemia (particularly, chronic period, transmigration period), malignant lymphoma (particularly, a first remission (high-risk group), a second remission and thereafter), multiple myeloma (particularly, an early period after onset), and the like; heart failure, angina pectoris, myocardial infarct, arrhythmia, valvulitis, cardiac muscle/pericardium diseases, congenital heart diseases (e.g., atrial septal defect, arterial canal patency, tetralogy of Fallot, etc.), arterial diseases (e.g., arteriosclerosis, aneurysm), vein diseases (e.g., phlebeurysm, etc.), lymphoduct diseases (e.g., lymphedema, etc.), and the like.

In another embodiment, diseases and disorders targeted by the present invention may be of the nervous system. Examples of such diseases or disorders include, but are not limited to, dementia, cerebral stroke and sequela thereof, cerebral tumor, spinal injury, and the like.

In another embodiment, diseases and disorders targeted by the present invention may be of the immune system. Examples of such diseases or disorders include, but are not limited to, T-cell deficiency syndrome, leukemia, and the like.

In another embodiment, diseases and disorders targeted by the present invention may be of the motor organ and the skeletal system. Examples of such diseases or disorders include, but are not limited to, fracture, osteoporosis, luxation of joints, subluxation, sprain, ligament injury, osteoarthritis, osteosarcoma, Ewing's sarcoma, myodystrophy, osteogenesis imperfecta, osteochondrodysplasia, and the like.

In another embodiment, diseases and disorders targeted by the present invention may be of the skin system. Examples of such diseases or disorders include, but are not limited to, atrichia, melanoma, cutis malignant lympoma, hemangiosarcoma, histiocytosis, hydroa, pustulosis, dermatitis, eczema, and the like.

In another embodiment, diseases and disorders targeted by the present invention may be of the endocrine system. Examples of such diseases or disorders include, but are not limited to, hypothalamus/hypophysis diseases, thyroid gland diseases, accessory thyroid gland (parathyroid) diseases, adrenal cortex/medulla diseases, saccharometabolism abnormality, lipid metabolism abnormality, protein metabolism abnormality, nucleic acid metabolism abnormality, inborn error of metabolism (phenylketonuria, galactosemia, homocystinuria, maple syrup urine disease), analbuminemia, lack of ascorbic acid synthetic ability, hyperbilirubinemia, hyperbilirubinuria, kallikrein deficiency, mast cell deficiency, diabetes insipidus, vasopressin secretion abnormality, dwarfism, Wolman's disease (acid lipase deficiency)), mucopolysaccharidosis VI, and the like.

In another embodiment, diseases and disorders targeted by the present invention may be of the respiratory system. Examples of such diseases or disorders include, but are not limited to, pulmonary diseases (e.g., pneumonia, lung cancer, etc.), bronchial diseases, and the like.

In another embodiment, diseases and disorders targeted by the present invention may be of the digestive system. Examples of such diseases or disorders include, but are not limited to, esophagial diseases (e.g., esophagial cancer, etc.), stomach/duodenum diseases (e.g., stomach cancer, duodenum cancer, etc.), small intestine diseases/large intestine diseases (e.g., polyps of the colon, colon cancer, rectal cancer, etc.), bile duct diseases, liver diseases (e.g., liver cirrhosis, hepatitis (A, B, C, D, E, etc.), fulminant hepatitis, chronic hepatitis, primary liver cancer, alcoholic liver disorders, drug induced liver disorders, etc.), pancreatic diseases (acute pancreatitis, chronic pancreatitis, pancreas cancer, cystic pancreas diseases, etc.), peritoneum/abdominal wall/diaphragm diseases (hernia, etc.), Hirschsprung's disease, and the like.

In another embodiment, diseases and disorders targeted by the present invention may be of the urinary system. Examples of such diseases or disorders include, but are not limited to, kidney diseases (e.g., renal failure, primary glomerulus diseases, renovascular disorders, tubular function abnormality, interstitial kidney diseases, kidney disorders due to systemic diseases, kidney cancer, etc.), bladder diseases (e.g., cystitis, bladder cancer, etc.), and the like.

In another embodiment, diseases and disorders targeted by the present invention may be of the genital system. Examples of such diseases or disorders include, but are not limited to, male genital organ diseases (e.g., male sterility, prostatomegaly, prostate cancer, testicular cancer, etc.), female genital organ diseases (e.g., female sterility, ovary function disorders, hysteromyoma, adenomyosis uteri, uterine cancer, endometriosis, ovarian cancer, villosity diseases, etc.), and the like.

As used herein, the term "effective amount for diagnosis, prevention, treatment, or prognosis" refers to an amount which is recognized as being therapeutically effective for diagnosis, prevention, treatment (or therapy), or prognosis. Such an amount can be determined by those skilled in the art using techniques well known and considering various parameters.

In another embodiment, the present invention may be used in therapy, treatment, or improvement for cosmetic purposes. Such cosmetic purposes include, cosmetic therapy for postoperative or posttraumatic deformation and congenital deformation as well as pure cosmetic purposes to healthy conditions. The present invention may be applied to, for example, without limitation, a technique for increasing breast tissue (breast augmentation), a technique for increasing cheek or upper and lower eyelids to compensate for a hollow, and a technique for increasing tissue to compensate for tissue atrophy after facial hemiatrophy or facial paralysis, or funnel breast. Further, the present invention may be applied to, for example, without limitation, rhinoplasty, reduction rhinoplasty, genioplasty (tissue augmentation), metopeplasty (tissue augmentation), auriclular chondroplasty for deformation/malformation of auricle, such as microtia, and the like.

When the present invention is used as a medicament, the medicament may further comprise a pharmaceutically acceptable carrier. Any pharmaceutically acceptable carrier known in the art may be used in the medicament of the present invention.

Examples of a pharmaceutical acceptable carrier or a suitable formulation material include, but are not limited to, antioxidants, preservatives, colorants, flavoring agents, diluents, emulsifiers, suspending agents, solvents, fillers, bulky agents, buffers, delivery vehicles, and/or pharmaceutical adjuvants. Representatively, a medicament of the present invention is administered in the form of a composition comprising a cell of the present invention and other active ingredients, with at least one physiologically acceptable carrier, excipient or diluent. For example, an appropriate vehicle may be an injection solution, physiological solution, or artificial cerebrospinal fluid, which can be supplemented with other substances which are commonly used for compositions for parenteral delivery.

Acceptable carriers, excipients or stabilizers used herein preferably are nontoxic to recipients and are preferably inert at the dosages and concentrations employed, and preferably include phosphate, citrate, or other organic acids; ascorbic acid, α-tocopherol; low molecular weight polypeptides; proteins (e.g., serum albumin, gelatin, or immunoglobulins); hydrophilic polymers (e.g., polyvinylpyrrolidone); amino acids (e.g., glycine, glutamine, asparagine, arginine or lysine); monosaccharides, disaccharides, and other carbohydrates (glucose, mannose, or dextrins); chelating agents (e.g., EDTA); sugar alcohols (e.g., mannitol or sorbitol); salt-forming counterions (e.g., sodium); and/or nonionic surfactants (e.g., Tween, pluronics or polyethylene glycol (PEG)).

Examples of appropriate carriers include neutral buffered saline or saline mixed with serum albumin. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

General techniques for preparing the medicament composition of the present invention will be described below. Note that animal drug compositions, quasi-drug compositions, marine drug compositions, food compositions, cosmetic compositions, and the like can be produced by known techniques.

The cell and the like of the present invention can be optionally mixed with a pharmaceutically acceptable carrier and can be parenterally administered as liquid formulations (e.g., injections, suspensions, solutions, spray agents, etc.). Examples of pharmaceutically acceptable carriers include excipients, lubricants, binders, disintegrants, disintegration inhibitors, absorption promoters, adsorbers, moisturizing agents, solvents, solubilizing agents, suspending agents, isotonic agents, buffers, soothing agents and the like. Additives for formulations, such as antiseptics, antioxidants, colorants, sweeteners, and the like can be optionally used. The composition of the present invention can be mixed with substances other than the polynucleotides, polypeptides, and the like of the present invention. Examples of parenteral routes of administration include, but are not limited to, intravenous, intramuscular, subcutaneous, intradermal, intramucosal, intrarectal, intravaginal, topically, percutaneous routes, and the like. When systemically administered, a medicament for use in the present invention may be in the form of a pyrogen-free, pharmaceutically acceptable aqueous solution. The preparation of such pharmaceutically acceptable compositions, with due regard to pH, isotonicity, stability and the like, is within the skill of the art.

Preferable examples of solvents in liquid formulations include injection solutions, alcohols, propyleneglycol, macrogol, sesame oil, corn oil, and the like.

Preferable examples of solubilizing agents in liquid formulations include, but are not limited to, polyethyleneglycol, propyleneglycol, D-mannitol, benzyl benzoate, ethanol, trisaminomethane, cholesterol, triethanolamine, sodium carbonate, sodium citrate, and the like.

Preferable examples of suspending agents in liquid formulations include surfactants (e.g., stearyltriethanolamine, sodium lauryl sulfate, lauryl amino propionic acid, lecithin, benzalkonium chloride, benzethonium chloride, glycerin monostearate, etc.), hydrophilic macromolecule (e.g., polyvinyl alcohol, polyvinylpyrrolidone, carboxymethylcellulose sodium, methylcellulose, hydroxymethylcellulose, hydroxyethylcellulose, hydroxyethylcellulose, hydroxypropylcellulose, etc.), and the like.

Preferable examples of isotonic agents in liquid formulations include, but are not limited to, sodium chloride, glycerin, D-mannitol, and the like.

Preferable examples of buffers in liquid formulations include, but are not limited to, phosphate, acetate, carbonate, citrate, and the like.

Preferable examples of soothing agents in liquid formulations include, but are not limited to, benzyl alcohol, benzalkonium chloride, procaine hydrochloride, and the like.

Preferable examples of antiseptics in liquid formulations include, but are not limited to, parahydroxybenzoate esters, chlorobutanol, benzyl alcohol, 2-phenylethylalcohol, dehydroacetic acid, sorbic acid, and the like.

Preferable examples of antioxidants in liquid formulations include, but are not limited to, sulfite, ascorbic acid, α-tocopherol, cysteine, and the like.

When liquid agents and suspensions are prepared as injections, they are sterilized and are preferably isotonic with the blood or a medium at an injection site for other purposes. Typically, these agents are made aseptic by filtration using a bacteria-retaining filter or the like, mixing with a bactericide or, irradiation, or the like. Following this treatment, these agents may be made solid by lyophilization or the like. Immediately before use, sterile water or sterile injection diluent (aqueous lidocaine hydrochloride solution, physiological saline, aqueous glucose solution, ethanol or a mixture thereof, etc.) may be added.

The medicament composition of the present invention may further comprise a colorant, a preservative, an aromatic chemical, a flavor, a sweetener, or other drugs.

The amount of a composition used in the treatment method of the present invention can be easily determined by those skilled in the art with reference to the purpose of use, target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patient's age, weight, sex, and case history, the progression of the therapy, and the like. Examples of the frequency include once per day to several months (e.g., once per week to once per month). Preferably, administration is performed once per week to month with reference to the progression. A dose can be determined by estimating an amount which is required by a site to be treated.

As used herein, the term "instructions" describe a method of administering a medicament, a method for diagnosis, or the like of the present invention for persons who administer, or are administered, the medicament or the like or persons who diagnose or are diagnosed (e.g., physicians, patients, and the like). The instructions contain a statement indicating an appropriate method for administering a diagnostic, a medicament, or the like of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly stating that the instructions are approved by the authority. The instructions are a so-called package insert and are typically provided in paper media. The instructions are not so limited and may be provided in the form of electronic media (e.g., web sites, electronic mails, and the like provided on the Internet).

The judgment of termination of treatment with a method of the present invention may be supported by a result of a standard clinical laboratory test using commercially available assays or instruments or extinction of a clinical symptom characteristic to a disease relevant to the intended treatment (e.g., bone diseases, heart diseases, neurological diseases, etc.) or recovery of cosmetic states (e.g., recovery of appearance, etc.). Therapy may be resumed due to the relapse of diseases associated with the deficiency of differentiated cells or the like (e.g., neurological diseases) or the damage of the cosmetic state.

The present invention also provides a pharmaceutical package or kit comprising one or more containers filled with one or more pharmaceutical compositions. A notice in a form defined by a government agency which regulates the production, use or sale of pharmaceutical products or biological products may be arbitrarily attached to such a container, representing the approval of the government agency relating to production, use or sale with respect to administration to humans. The kit may comprise an injecting device.

Toxicity studies may be carried out by using a variety of animal models (such as mice, rabbits, non-rodents). In these animal models, observation of general conditions, body weight, amount of feed, amount of drinking water, as well as inspection of blood test, blood biochemical test, urine test, and ophthalmologic test and the like are conducted. A variety of tests are well known in the art, and include but are not limited to the following:

Hematologic test: red blood cell number, white blood cell number, platelet number, hemoglobin, hematocrit, hemogram (percentage for white blood cell type), other reticulocyte number, prothrombin time, activated partial thromboplastin time and the like are conducted. For example, a blood cell composition is measured as follows:

(1) an agent is administered to a mouse (a non-treated control mouse should also be measured); (2) a blood sample is taken via the caudal vein from one of each treated mouse group in a periodic manner; and (3) the above-mentioned sample is analyzed for red blood cell and white blood cell numbers, blood cell composition, and the ratio of lymphoid cells to polymorphonuclear cells. Results of each dosage regimen and control show whether toxicity is present or not.

Blood biochemical test: measurements of serum (plasma) protein, albumin, A/C ratio, protein fractionation, glucose, cholesterol, triglyceride, bilirubin, urea nitrogen, creatinine, transaminase (ASAT(GOT), ALAT(GPT)), alkali phosphatase, electrolyte (sodium, potassium, chloride, calcium, inorganic phosphorus and the like).

Urinalysis: measurements of urine volume, pH, protein, carbohydrate, ketone body, bilirubin, occult blood, sediment, specific gravity or osmotic pressure, electrolyte (sodium, potassium and the like).

Ophthalmologic test: Gross and ophthalmoscope are used to analyze anterior eye, optic media, and fundus oculi.

At the end of each toxicity study, a further study may be carried out by sacrificing the animal (preferably, in accordance with American Veterinary Medical Association guidelines Report of the American Veterinary Medical Assoc. Panel on Euthanasia, (1993) J. Am. Vet. Med. Assoc. 202: 229-249). Thereafter, a representative animal from each treatment group may be tested by viewing the whole body for direct evidence of transitions, abnormal diseases or toxicity. A global abnormality in tissue is described and the tissue is hisotologically tested. A compound causing a reduction in weight or a reduction in blood components is not preferable as are medicaments having an adverse action on major organs. In general, the greater the adverse action, the less preferable the medicament.

DESCRIPTION OF PREFERRED EMBODIMENTS

Hereinafter, preferred embodiments of the present invention will be described. The following embodiments are provided for a better understanding of the present invention and the scope of the present invention should not be limited to the following description. It will be clearly appreciated by those skilled in the art that variations and modifications can be made without departing from the scope of the present invention with reference to the specification.

(Method for Preparing a Stem Cell from an Aspirate Derived from Liposuction)

In one aspect of the present invention, the present invention provides a method for preparing a stem cell from an aspirate from liposuction, comprising A) obtaining an aspirate from liposuction; B) subjecting the aspirate from liposuction to centrifugation to obtain a cellular fraction; C) subjecting the cellular fraction to cell separation by specific gravity such as density gradient centrifugation; and D) collecting a cell layer having lower specific gravity than the red blood cell. The aspirate from liposuction as used in the inventive method include, but not limited to, a liquid which is aspirated together with fat during liposuction (including, but not limited to, for example, Tumescent solution and blood), waste liquid produced in washing the aspirated fat with a liquid.

Adipose-derived precursor cells can be isolated from the fat portion of aspirates (lipoaspirates) from liposuction as follows (e.g., WO00/53795; WO03/022988; WO01/62901; Zuk, P. A., et al., Tissue Engineering, Vol. 7, 211-228, 2001; Zuk, P. A., et al., Molecular Biology of the Cell Vol. 13, 4279-4295, 2002; or modifications thereof. Specifically, for example, (1) suctioned fat is washed well with physiological saline using a 1-liter separatory funnel; (2) the sufficient separation of the suctioned fat in the upper layer from the physiological saline in the lower layer is confirmed, and thereafter, the lower layer is discarded. This procedure is repeated until the physiological saline becomes substantially transparent when viewed with the naked eye; (3) 0.075% collagenase/PBS is added in an amount equal to that of the suctioned fat, followed by incubation at 37° C. for 30 minutes while stirring well; (4) an equal amount of 10% serum-supplemented DMEM is added to the above-described sample; (5) the sample is centrifuged at 1200×g for 10 minutes; (6) the resultant pellet is suspended in 0.16 M $N_4Cl$/PBS, followed by incubation at room temperature for 10 minutes; (7) the sample is subjected to suction filtration using a 100 μm-diameter mesh; and (8) the resultant filtrate is centrifuged at 1200×g for 5 minutes. The above-described protocol may be scaled up or down by those skilled in the art, depending on the amount of formulation.

On the other hand, adipose-derived precursor cells can be isolated from the liquid portion of aspirates (liquid aspirates) from liposuction, for example, as follows: (1) a liquid portion of aspirates from liposuction is prepared; (2) the liquid portion is centrifuged to obtain a cell fraction; (3) the cell fraction is subjected to density gradient centrifugation, and cell separation is performed based on the specific gravity; and (4) cells are collected from a cell layer having a specific gravity lower than that of an erythrocyte. The liquid portion of aspirates may be prepared using physiological saline or Ringer's injection. The centrifugation may be performed at a rate of about 800×g or less, or alternatively, about 400×g or more. The density gradient centrifugation is performed at a rate of about 370×g to 1,100×g. The density gradient centrifugation is performed using a medium having a specific gravity (20° C.) of about 1.076 to 1.078 g/ml. The medium used in the density gradient centrifugation may be Ficoll™, Percoll™, or sucrose. The specific gravity of the collected cell layer may be in the range of about 1.050 to 1.075. The cell layer may be collected using a pipette.

A method for suctioning fat may be carried out using technology well known to those skilled in the art. Apparatuses used in a method for suctioning fat include but not limited to Keisei SAL PUMP (SAL 76-A, Keisei Ika-Kogyo, Hongo 3-19-6, Bunkyo, Tokyo, Japan). In a case of a human, a liquid such as a saline containing 0.0001% adrenalin is infused into fat tissue with an equal to double volume of that of fat to be aspirated, and thereafter cannulae having 2-3 mm of inner diameter (aspirating tube made of metal) is used for suctioning about ~250-900 mmHg of negative pressure.

Liquid to be used for washing aspirated adipocytes is usually saline. However, any liquid other than saline may be used as long as such liquid has no adverse effect on stem cells to be isolated. Specifically, for example, any isotonic solution such as Ringer's solution, and mammalian cell culture medium (for example, DMEM, MEM, M199 and MCDB153 and the like) may be used in the present invention.

When preparing stem cells from aspirate from liposuction, it may be possible to optionally subject such an aspirate from liposuction to an enzyme such as collagenase. However, the amount of collagen included in such an aspirate from liposuction is relatively low in comparison with that of fat tissue, when using such aspirate from liposuction as a source for preparing stem cells, the time required for collagenase treatment and/or the amount of enzymes required for the enzyme treatment is relatively lower than that required for fat tissue.

In the step of obtaining a cell fraction by centrifuging aspirate from liposuction, any condition may be used as long as such a cell fraction and other components (for example, plasma, saline contaminated in operation, anesthetic, hemostyptic, lipid components exudated from broken adipocytes) are separated. For example, centrifugation at 400-800×g for about 5-15 minutes can be used.

In the step of separating cells by specific gravity, for example isolated cell fractions may be subjected to density gradient centrifugation. Any usable medium for density gradient centrifugation may be used as such a medium. Preferable medium may have a specific gravity of 1.076-1.078 g/ml. Further, pH of preferable medium is between 4.5 and 7.5. Endotoxin level of preferable medium may be 0.12 EU/ml or less. Typical medium includes sucrose, Ficoll (copolymer of sucrose and epichlorohydrin) and Percoll (colloidal silica product having film of polyvinyl pyrrolidone). Ficoll is commercially available as for example Ficoll-Paque PLUS (Pharmacia Biotech Japan, Tokyo, Japan), Histopaque-1077 (SIGMA-Aldrich Japan, Tokyo, Japan) and the like. Percoll is commercially available as Percoll (SIGMA-Aldrich Japan, Tokyo, Japan).

Condition of centrifugation by specific gravity can be as follows: when Ficoll-Paque PLUS is used as a medium, 400×g, 30-40 minutes is used, when Histopaque-1077 is used as a medium, 370 cg and about 30 minutes is used. When Lymphoprep is used as a medium, conditions include but are not limited to 800×g, about 20 minutes and 1,100×g and about 10 minutes and the like.

In a centrifugation at the specific gravity to be used, the most abundant cells are usually erythrocytes, and can be confirmed by observing a red cell layer. Stem cells have less specific gravity than the erythrocytes, when separating the stem cells, cell layer having lower specific gravity than that of erythrocytes are collected. Preferably, cell layers having a range of specific gravity of 1.050-1.075 are collected.

An approximate specific gravity of cells can be tested by preparing density gradient centrifugation medium such as Percoll, Readygrad in sodium chloride solution or sucrose solution, centrifuging collected cells with densitimer marker beads, and confirming which layer contains cells among layers separated into five to ten layers.

Further, collection of cells separated into layers may be conducted, for example, using a pipette.

In a centrifugation by specific gravity, a cell separator such as blood component separation apparatus ASTEC204, Amco) can be used.

In another aspect of the present invention, the method for preparing a stem cell of the present invention comprises: A) obtaining material from liposuction; and B) subjecting the material from liposuction to centrifugation to obtain a cell fraction without isolation of fat tissue. The method may further comprise filtering the cell fraction to obtain stem cells. The present method may further comprise the step of subjecting the material to a condition where at least a portion of cells are separated from the material.

Material from liposuction is any material obtainable when a liposuction operation is conducted. Such material contains fat, adipocytes, liquid, extracellular matrices such as collagens, and the like. In the present invention it has been found that such material from liposuction in general in addition to aspirate from liposuction also contains abundant stem cells or precursor cells. Therefore, material from liposuction in general is a good source for preparing stem cells. Such effects could have not been expected in the art.

A condition where fat tissue is separated from cells, may be any condition as long as fat tissue is separated from cells and facilitates the isolation of cells. Such conditions include but are not limited to degradation of extracellular matrices such as adding a collagenase, such as those available from Wako (collagenase for cell dispersion, 032-10534). Such a collagenase is dissolved in PBS at the concentration of 0.075%, and warm the solution to 37° C. and added to an equal volume of fat. Agitator is used for agitating the sample at 37° C. at 80 rpm for 30 minutes.

In the centrifugation step as used in the present invention, the present invention may further comprise removing supernatant to obtain a cell layer.

Preferably, the present method may further comprise the step of removing supernatant in step B) or filtering the material from the step B), in order to remove remaining fat masses. Any filter may be used for this purpose, as long as no clogging causes.

Preferably, the present method further comprises the step of removing blood cells, in order to achieve higher degree of stem cell purity. However, such blood cells may be removed by subsequently culture on a dish and subjecting the cell masses to passage resulting the cells with more than 80%, preferably more than 90% of stem cells. This is also surprising effect, which has not been expected from the prior art. Such blood cells may be removed by the step of removing blood cells comprises adding a component of degrading blood cells In a preferable embodiment of the present invention, the present invention provides a method for preparing a stem cell comprising i) obtaining material from liposuction; ii) subjecting the material to a condition where fat tissue is separated from cells, preferably without isolation of fat tissue; iii) subjecting the material to centrifugation; iv) adding a component degrading blood cells to the material and agitating the material; v) subjecting the material to centrifugation to obtain a pellet; vi) aspirating supernatant of the material from the pellet.

The material from liposuction used in the present invention usually includes an aspirate from liposuction and fat, however, it was found that when treated according to the preset invention, the material contains many more stem cells than that found in an aspirate.

Preferably, said condition in said step ii) comprises adding a collagenase.

Preferably, the present method may further comprise the step of subjecting the material to said condition comprises maintaining an aspirate from the liposuction.

Preferably, the material from liposuction used in the present invention, may further comprises an aspirate from liposuction and fat.

In another embodiment, the centrifugation in said step iii) is conducted at 400-1200×g. Usually 400×g or 800×g is used.

In another embodiment, said component degrading blood cells comprises ammonium chloride and potassium bicarbonate.

In another embodiment, said ammonium chloride is comprised in the component at 100 mM to 200 mM, preferably at about 155 mM. In another embodiment, said potassium bicarbonate is comprised in the component at 5 mM to 20 mM, preferably about 10 mM. Preferably, the combination of the two is advantageously used.

In another embodiment, said centrifugation in said step v) is conducted at 400-1200×g.

The pellet obtained by the present invention includes a number of stem cells, or precursor cells. These cells have been demonstrated to have capability of differentiation into a number of differentiated cells, such as bone, cartilage, fat and the like.

In the present invention, erythrocytes are preferably removed, however, such removal is not always necessary, as the stem cells of the present invention prepared without such removal step also showed significant differentiation and proliferation activities.

Media used for culturing such collected cells include, but not limited to, for example, DMEM, M199, MEM, HBSS, Ham's F12, BME, RPMI1640, MCDB104, MCDB153 (KGM) and the like. Preferable media include DMEM and M199.

Collected cells are heterogeneous cell populations and include stem cells expressing CD13, CD29, CD44, CD49d, CD71, CD73, CD90, CD105, CD151, and may further include stem cells expressing either of CD31 or CD34, or both.

In one aspect of the present invention, collected cells are cultured under a number of conditions to obtain a variety of cells such as vascular endothelial cells, neurological cells, smooth muscle cells, cardiac muscle cells, skeletal muscle cells, cartilage cells, bone cells, adipocytes, ligament cells, and stroma cells and the like.

Such conditions are known in the art and include:

Seed obtained cells onto a 60 mm-dish at a concentration of $1.8 \times 10^6$ cells in DMEM medium.

One to two week culture render the cells into subconfluent states, and thereafter the cells are subjected to a fat differentiation inducing medium, a cartilage differentiation inducing medium or bone differentiation inducing medium and continuing culture for about 2-4 weeks.

Exemplary adipogenesis medium may be DMEM supplemented with 10% FBS, containing 0.5 mM IBMX, 1 μM dexamethasone, 10 μM insulin, 200 μM indomethacine, and 1% AMAM.

Exemplary osteogenesis medium may be DMEM supplemented with 10% FBS and 5% horse serum, containing 1 μM dexamethasone, 50 μM ascorbate-2-phosphate, 10 mM β-glycerophosphate, and 1% ABAM.

Exemplary chondrogenesis medium may be DMEM supplemented with 1% FBS, containing 6.25 μg/ml insulin, 6.25 μg/ml transferrin, 10 ng/ml TGF β1, 50 nM ascorbate-2-phosphate, and 1% ABAM. ABAM antibiotic-antimycotic solution is available from Gibco (ABAM; cat. no. 600-5240).

Evaluating the cells after the induction using Oil-Red O for fat tissue, Alcian blue for cartilage tissue, and von Kossa staining for bone tissue.

Further, in the present invention, the following methods can be used to separate and collect vascular endothelial precursor cells from a collected cell group.

For example, a collected cell group is cultured on a 1% gelatin coated culture dish using a medium for culturing vascular endothelial cells for about 4-5 days. After the culture, the cell group is detached using 0.25% trypsin, and is reacted with anti-PECAM-1 beads to separate cells only reacted with the antibody using MACS (magnetic cell separation system) or FACS (flow cytometry). Separated cells are cultured on a 1% gelatin coated culture dish using a medium for culturing vascular endothelial cells. In order to exclude contaminating fibroblasts and the like, using the property of vascular endothelial cells where the cells are more detachable than the other cells, 0.25% trypsin is reacted with the cells for about 30-40 seconds and only the detached cells are collected and cultured in a different culture dish, to allow isolation of differentiated vascular endothelial precursor cells (see, for example, Hutley L J, et al: Human adipose tissue endothelial cells promote preadipocyte proliferation. Am. J. Physiol. Endocrinol. Metab. 2001 November; 281(5): E1037-44).

In a further aspect of the present invention, the present invention provides a system for preparing a stem cell comprising A) means for obtaining an aspirate from liposuction; B) means for separating the aspirate from liposuction to obtain a cell fraction; and C) means for subjecting the cell fraction to separation by specific gravity such as density gradient centrifugation for cell separation. The present system allows preparation of stem cells in a simple manner, in a large amount, and in a manner which may be automated.

In a different aspect, the present invention provides a system for preparing a stem cell comprising: A) means for obtaining material from liposuction; and B) means for subjecting the material from liposuction to centrifugation to obtain a cell fraction without isolation of fat tissue.

In a yet different aspect, the present invention provides a system for preparing a stem cell comprising: i) means for obtaining material from liposuction; ii) means for subjecting the material to a condition where at least a portion of cells are separated from the material, preferably without isolation of fat tissue; iii) means for subjecting the material to centrifugation; iv) a component degrading blood cells to the material and agitating the material; v) means for subjecting the material to centrifugation to obtain a pellet; and vi) means for aspirating supernatant of the material from the pellet.

Means for obtaining aspirate from liposuction include means for aspirating fat using a vacuum from the body. For example, such means include but are not limited to: fat aspiration operations (fat aspiration operation using a manual vacuum injector, and vacuum aspirator and the like), and defatting operations by skin incision.

Means for separating the aspirate from liposuction to obtain a cell fraction, and means for subjecting the cell fraction to separation by specific gravity such as density gradient centrifugation for cell separation, include, but are not limited to a centrifuge. When obtaining a cell fraction by centrifugation of aspirate from liposuction, conditions include 200-1200×g, for 30-60 minutes, preferably 260-900×g, for 3-30 minutes, more preferably 400-800×g, for 3-15 minutes, and most preferably 400×g, for 5-10 minutes. When Ficoll used for cell separation by specific gravity using density gradient centrifugation, conditions may be 200-1200×g, for 10-60 minutes, preferably 260-900×g, for 10-60 minutes, more preferably 400-800×g, for 10-40 minutes, and most preferably 400×g, for 30-40 minutes. Further, the present system optionally includes means for collecting a cell layer of a specific gravity of interest. Preferably, collected cell layers are those having less specific gravity than that of an erythrocyte. Such means include but are not limited to a manual pipetter, manual aspirator, automatic pipetter, and automatic aspirator and the like.

The stem cells of the present invention may be used to obtain a variety of differentiated cells and/or precursor cells. Specific procedures are described below.

(Method for Preparing Differentiated Cells)

In one aspect, the present invention provides a method for preparing differentiated cells from stem cells. Such differentiated cells obtainable from the stem cells, may be not only ultimately differentiated cells, but also precursor cells.

Methods for preparing differentiated cells from a stem cell derived from an aspirate from liposuction include (1) a method for adding a differentiation inducer such as dexamethasone, into a culture medium; and (2) a method for culturing the stem cell with a differentiated cell corresponding to the site of interest.

(Method for Adding a Differentiation Inducer into a Culture Medium for Inducing Stem Cell Differentiation)

A cell mixture of the present invention may further comprise an agent for promoting differentiation into a differentiated cell corresponding to a desired site. Such an agent may be any one which is known or confirmed to promote differentiation into a differentiated cell corresponding to a desired site. Examples of preferable differentiation promoting agents include, but are not limited to, adrenocortical steroids (e.g., dexamethasone, etc.), insulin, glucose, indomethacin, isobutyl-methylxanthine (IBMX), ascorbate-2-phosphate (ascorbate-2-phosphate), ascorbic acid and a derivative thereof, glycerophosphate, estrogen and a derivative thereof, progesterone and a derivative thereof, androgen and a derivative thereof, growth factors (e.g., αFGF, βFGF, EGF, IGF, TGF-β, ECGF, BMP, PDGF, etc.), a pituitary gland extract, a pineal body extract, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hydroxyurea (HU), cytosine arabinoside (AraC), mitomycin C (MMC), sodium butyrate (NaBu), polybrene, selenium, and the like.

For the cell mixture of the present invention, any culture medium may be used as long as mixed cells can be maintained and differentiation into a differentiated cell corresponding to a desired site can be maintained. Examples of such a culture medium include, but are not limited to, DMEM, M199, MEM, HBSS (Hanks' Balanced Salt Solution), Ham's F12, BME, RPMI1640, MCDB104, MCDB153 (KGM), and the like. Such a culture medium may be supplemented with adrenocortical steroids (e.g., dexamethasone (dexamethasone), etc.), insulin, glucose, indomethacin, isobutyl-methylxanthine (IBMX), ascorbate-2-phosphate (ascorbate-2-phosphate), ascorbic acid and a derivative thereof, glycerophosphate (glycerophosphate), estrogen and a derivative thereof, progesterone and a derivative thereof, androgen and a derivative thereof, growth factors (e.g., αFGF, βFGF, EGF, IGF, TGF-β, ECGF, BMP, PDGF, etc.), an extract of pituitary gland, an extract of pineal body, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hyroxyurea (HU), cytosine arabinoside (AraC), mitomycin C (MMC), sodium butyrate (NaBu), polybrene, selenium, and the like, alone or in combination.

Conditions for differentiation induction into a fat cell from a stem cell derived from an aspirate from liposuction include, but are not limited to, for example, culturing the stem cell in a DMEM medium added with isobutyl-methyl xanthine, dexamethasone, insulin, and indomethacin.

Conditions for differentiation induction into a cartilage cell from a stem cell derived from an aspirate from liposuction include, but are not limited to, for example, culturing the stem cell in a DMEM added with insulin, ascorbate-2-phosphate, and TGF-beta 1.

Conditions for differentiation induction into a bone cell from a stem cell derived from an aspirate from liposuction include, but are not limited to, for example, culturing the stem cell in a DMEM added with dexamethasone, ascorpate-2-phosphate, and beta-glycerophosphate.

Conditions for differentiation induction into a muscle cell from a stem cell derived from an aspirate from liposuction include, but are not limited to, for example, culturing the stem cell in a DMEM supplemented with 10% Fetal bovine serum (FBS) and 5% horse serum (HS) added with dexamethasone, hydrocortisone.

(Induction of Differentiation by Simultaneous Culture of a Stem Cell and a Differentiated Cell Corresponding to the Site of Interest)

This simultaneous culture of a stem cell and a differentiated cell corresponding to the site of interest allows production of a certain amount of differentiated cells having desired properties, preferably in a homogeneous manner. The present method comprises A) obtaining a mixture by mixing a) an adipose-derived precursor cell, and b) a differentiated cell corresponding to a desired site; and B) culturing the mixture under sufficient conditions which allow the adipose-derived precursor cell to differentiate A differentiated cell corresponding to a desired site can be prepared using techniques well known in the art. Alternatively, such a differentiated cell may be available from commercially available cell lines (e.g., cell lines obtained from the ATCC or the like, etc.). Such a differentiated cell may be obtained from primary cultured cells from a subject in need of implantation (e.g., hepatic cells, renal cells, adipocytes, bone cells, chondrocytes, etc.). Techniques for primary culture and cell line culture are well known in the art as described in, for example, Hiroshi Hatanaka & Akira Asano, eds., "AMBO Manuaru Saibo Kenkyuho [AMBO Manual of Cell Study Methods]", TaKaRa; Toshio Watanabe, ed., "Baio Jikken Irasutoreiteddo (6) Sukusuku Sodate Saibo Baiyo [Illustrated Culture Experiments—Cells grow quickly]", Shujun sha (1996); and the like, which are herein incorporated by reference.

In the present invention, any differentiated cells may be used as long as the cells correspond to a desired site, and preferably, mesenchymal cells including but not limited to adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, pancreas cells, and renal cells and the like. Such differentiated cells may be identified cells, however, even if the properties of such cells are unknown, such cells may be used for preparing cells corresponding to a desired site using separation technology such as FACS.

Examples of markers useful for the determination of a cell corresponding to such a desired site include, but are not limited to, (1) fat: the presence of triglycerides within the cytoplasm, OilRed-O staining, glycerophosphatedehydrogenase (Glycerophosphate dehydrogenase=GPDH) activity, GLUT4 within the cytoplasm, Ap2 (fatty acid binding protein), LPL (lipoprotein lipase), PPARγ1,2 (peroxisome growth activating receptor γ1,2), and the expression of leptin; (2) bone cell, bone tissue: the presence of alkaliphosphatase, the confirmation of the degree of bone calcification (precipitation of calcium), and the expression of osteocalcin, osteopontin, or osteonectin; (3) chondrocyte, cartilage tissue: the presence of mucopolysaccharides, the expression/presence of type II collagen, chondroitin-4-sulfate; (4) skeletal muscle cells: the presence of abundant myosin within the cytoplasm; and the like. FACS protocols are described in, for example, Nakauchi, ed., "Furosaitometori Jiyujizai [Master of Flow cytometery]", Special Issue, Saibokogaku [Cell Engineering] (Shujunsha), 1999; and the like, which is herein incorporated by reference.

A cell mixture of the present invention may further comprise an agent for promoting differentiation into a differentiated cell corresponding to a desired site. Such an agent may be any one which is known or confirmed to promote differentiation into a differentiated cell corresponding to a desired site. Examples of preferable differentiation promoting agents include, but are not limited to, adrenocortical steroids (e.g., dexamethasone, etc.), insulin, glucose, indomethacin, isobutyl-methylxanthine (IBMX), ascorbate-2-phosphate (ascorbate-2-phosphate), ascorbic acid and a derivative thereof, glycerophosphate, estrogen and a derivative thereof, progesterone and a derivative thereof, androgen and a derivative thereof, growth factors (e.g., αFGF, βFGF, EGF, IGF, TGF-β, ECGF, BMP, PDGF, etc.), a pituitary gland extract, a pineal body extract, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hydroxyurea (HU), cytosine arabinoside (AraC), mitomycin C (MMC), sodium butyrate (NaBu), polybrene, selenium, and the like.

For the cell mixture of the present invention, any culture medium may be used as long as mixed cells can be maintained and differentiated into a differentiated cell corresponding to a desired site. Examples of such a culture medium include, but are not limited to, DMEM, M199, MEM, HBSS (Hanks' Balanced Salt Solution), Ham's F12, BME, RPMI1640, MCDB104, MCDB153 (KGM), and the like. Such a culture medium may be supplemented with adrenocortical steroids (e.g., dexamethasone (dexamethasone), etc.), insulin, glucose, indomethacin, isobutyl-methylxanthine (IBMX), ascorbate-2-phosphate (ascorbate-2-phosphate), ascorbic acid and a derivative thereof, glycerophosphate (glycerophosphate), estrogen and a derivative thereof, progesterone and a derivative thereof, androgen and a derivative thereof, growth factors (e.g., αFGF, βFGF, EGF, IGF, TGF-β, ECGF, BMP, PDGF, etc.), an extract of pituitary gland, an extract of pineal body, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hyroxyurea (HU), cytosine arabinoside (AraC), mitomycin C (MMC), sodium butyrate (NaBu), polybrene, selenium, and the like, alone or in combination.

Accordingly, in another aspect, the present invention provides a cell mixture comprising a stem cell derived from aspirate from liposuction and a differentiated cell corresponding to a desired site. Such a mixture is useful for cell transplantation, and further has advantages such as that the amount of each component is required less than those using a single type cell as used in the prior art. In addition, additional advantages superior to the prior art include, for example, (1) not necessary to produce regenerated tissue ex vivo; (2) permissible to reproduce a larger tissue in a more definitive manner; (3) possible to carry out the method in a simple manner, in a shorter time period; (4) not necessary to conduct an operation with incision of an organ such as skin, and possible to administer (transplant) cells and/or tissues only by the use of a needle.

Cell mixture of the present invention are preferably those subjected to a condition sufficient for induction of differentiation of a stem cell into fat, however, the present invention is not limited to this. A cell mixture, after subject to a differentiation condition, may be used for direct transplantation, or differentiated into a tissue or organ.

(Cell Transplantation Composition)

In another aspect, the present invention provides a composition for cell transplantation (for example, tissue explant, and explant and a composition containing the same). This transplantation may be used for any purpose as long as it is used for treating or preventing a disease, disorder or abnormal condition associated with deficiency or deterioration of a differentiated cell corresponding to a desired site, or treating or ameliorating a cosmetic condition. Such transplantation includes preferably, but is not limited to, transplantation into a desired site, and the cell containing composition of the present invention may be administrated or transplanted to any desired site as long as treatment or prevention of such a desired site is eventually possible.

The mixing ratio of a stem cell from an aspirate from liposuction and a differentiated cell may be any ratio as long as the desired differentiation occurs, and usually about 1:10 to about 10:1, and preferably about 1:5 to about 5:1, and more preferably about 1:2 to about 2:1, and most preferably, approximately equal volumes of each cell are present. In the present cell mixture, the differentiated cells and the stem cell derived from an aspirate from liposuction used for transplantation may take any form and embodiments as described in the section "Method for preparing differentiated cells" as described herein above.

The differentiated cell and the adipose-derived precursor cell each are heterologous, allogenic, or isologous to a host into which they are implanted. Preferably, they are allogenic or isologous, and more preferably isologous. The present invention is not limited to this. Though not wishing to be bound by any theory, this is because it is possible to suppress immune rejection responses. However, if a rejection response is expected, the present invention may further comprise avoiding the rejection response. Procedures for avoiding rejection reactions are known in the art (see, for example, "Shin Gekagaku Taikei, Dai 12 Kan, Zoki Ishoku (Shinzo Ishoku-Hai Ishoku Gijutsuteki, Rinriteki Seibi kara Jisshi ni Mukete [New Whole Surgery, Vol. 12, Organ Transplantation (Heart Transplantation•Lung Transplantation From Technical and Ethical Improvements to Practice)" (Revised 3rd ed.), Nakayama Shoten]. Examples of such methods include, but are not limited to, a method using immunosuppressants or steroidal drugs, and the like. For example, there are currently the following immunosuppressants for preventing rejection reactions: "cyclosporine" (SANDIMMUNE/NEORAL); "tacrolimus" (PROGRAF); "azathioprine" (IMURAN); "steroid hormone" (prednine, methylprednine); and "T-cell antibodies" (OKT3, ATG, etc.). A method which is used worldwide as a preventive, immunosuppression therapy in many facilities, is the concurrent use of three drugs: cyclosporine, azathioprine, and a steroid hormone. An immunosuppressant is desirably administered concurrently with a pharmaceutical agent of the present invention. The present invention is not limited to this. An immunosuppressant may be administered before or after a regeneration/therapeutic method of the present invention as long as an immunosuppression effect can be achieved.

The differentiated cell and the adipose-derived precursor cell each are heterologous, allogenic, or isologous, preferably allogenic or isologous, and more preferably isologous. Though not wishing to be bound by any theory, this is because a differentiated cell and an adipose-derived precursor cell, which are allogenic or isologous (autologous) (preferably isologous), are likely to form a homogenous cell group.

The above-described cell mixture or composition may be provided as a medicament. Such a medicament may be used for treatment or prevention of diseases, disorders or abnormal conditions associated with the deficiency or deterioration of a differentiated cell corresponding to a desired site, or treatment or improvement of cosmetic conditions. The medicament of the present invention may comprise a pharmaceutically acceptable carrier in addition to the cell mixture or a composition comprising the same. As such a carrier, any carrier as described herein can be selected and used by those skilled in the art, depending on the purpose. Those skilled in the art will be able to modify the components to be contained in the present invention.

(Treatment and Prevention Using Cell Mixture)

In another aspect, the present invention provides a method for treatment or prevention of a disease, a disorder or an abnormal condition attributed to the deficiency of a differentiated cell, and method for treatment or improvement of a cosmetic condition. These methods comprise the steps of: A) providing a composition comprising: a) an adipose-derived precursor cell; and b) a differentiated cell corresponding to a desired site; and B) administering the composition to a subject. In the present methods, the differentiated cells and the stem cell derived from an aspirate from liposuction used for transplantation may take any form and embodiments as described in the section "Method for preparing differentiated cells" as described herein above.

Any administration method may be used including those known in the art in the present invention. For example, without limitation, the composition may be injected using a syringe, a catheter, a tube, or the like. Preferably, exemplary routes of administration include, but are not limited to, local injection (subcutaneous injection, intraorgan injection (e.g., muscle, fat, etc.), intravenous injection, intraarterial injection, administration onto tissue, and the like. The treatment or preventative method of the present invention by implantation has the following advantages over conventional techniques, for example, without limitation: (1) production of regenerated tissue outside the body (ex vivo production) is not required; (2) a larger tissue can be regenerated more reliably; (3) regeneration can be achieved simply and quickly; (4) an incision operation is not required for an organ, such as skin or the like, and cells and tissue can be administered (implanted or transplanted) by needle puncture; and the like.

(Use)

In another aspect, the present invention provides use of a mixture of a) an adipose-derived precursor cell and b) a differentiated cell corresponding to a desired site for treatment or prevention of diseases, disorders or abnormal conditions associated with the deficiency or deterioration of a differentiated cell corresponding to a desired site or treatment or improvement of cosmetic conditions for cell implantation. The differentiated cell and the adipose-derived precursor cell used in the cell mixture for implantation may be herein in any form as described in the "Methods for preparing differentiated cells" section.

Hereinafter, the present invention will be described by way of examples. The Examples described below are provided only for illustrative purposes. Accordingly, the scope of the present invention is not limited by the above-described embodiments or the examples below, except as by the appended claims.

EXAMPLES

Reagents used in the examples below were obtained from Wako Pure Chemical Industries or Sigma unless otherwise specified. Animals were cared for in compliance with the spirit of animal protection in accordance with "Principles of Laboratory Animal Care" prepared by National Society for Medical Research and "Guide for the Care and Use of Laboratory Animals" (NIH Publication No. 86-23, 1985 revised) prepared by Institute of Laboratory Animal Resource and published by National Institute of Health. Informed consent was obtained from human subjects before any experiment.

Example 1: Preparation of an Aspirate of Liposuction

An excess amount of Tumescent solution (saline containing 0.0001% adrenalin), which exceeds the amount of liposuction to be aspirated prior to the liposuction operation, was infused into hypodermic fat layer (tumescent method), and thereafter cannulae having 2-3 mm of inner diameter (made of metal with aspirator) are used for the liposuction operation. Liposuction operations are well known in the art, and for example, can be referred to in Biyo Seikei Shujutsu Practice 2 (Cosmetic Operation Practice 2), ed. Masanari ICHIDA, Ryusaburo TANINO, and Yoshiaki HOSAKA, published by BUNKODO, pp. 429-469, which is incorporated herein by reference in its entirety.

Aspirated fat was washed with saline. About five to ten liters of washed aspirate was generated, and the initial one to two liters thereof containing abundant cellular materials were used for the following processes.

Example 2: Preparation of a Stem Cell Suspension from an Aspirate of Liposuction The aspirates taken were processed as follows using either of the two methods to prepare stem cell suspension. The following two methods do not require processes using enzymes such as collagenases, the methods are distinct from conventional methods and stem cells from fat tissue prepared by conventional methods in that there is no contamination of enzymes such as collagenases.

(I) Preparation Method 1

1) A liquid portion of an aspirate from liposuction (typically, about 2 to 4 liters) was centrifuged at 400×g for 10 minutes.

2) The supernatant was discarded. Note that as the precipitated cells were likely to float, an aspirator was used to carefully perform suction without damaging the cells.

3) The pelleted cells (mostly, erythrocytes) were transferred to several 50-ml polypropylene tubes, followed by centrifugation (400×g, 5 min).

4) The supernatant was suctioned out. A total volume of 15 to 20 ml of pelleted cells was collected. When a large amount of matrix components was contained therein, the matrix components were filtered out using a 100-µm filter. Thereafter, centrifugation was performed as required.

5) Ficoll® (15 mL) was added to a 50-ml tube. Thereafter, 15 to 20 ml of the cell solution was added very slowly to form a layer thereon.

6) The tube was centrifuged at 400×g for 30 minutes (18 to 20° C.).

7) After centrifugation, the cell solution was separated into four layers: from the top, A layer (cell-free layer, transparent); B layer (mononuclear cell layer, pale red color); C layer (Ficoll layer, transparent); and D layer (erythrocyte layer, deep red) Adhesion cells including stem cells were contained in the B and C layers. The A layer was suctioned off. The B layer and the C layer (about 3 ml) were recovered as a cell suspension, which in turn was transferred to a 50-ml tube.

8) Serum-supplemented PBS (PBS supplemented with 10% FBS or 10% human serum) was added to the recovered cell suspension to a volume of 50 ml. The mixture was mixed by pipetting, and the mixture was then centrifuged (400×g, 5 minutes).

9) The supernatant was suctioned off. Serum-supplemented PBS was added again to a volume of 50 ml. The mixture was mixed by pipetting, and the mixture was then centrifuged (400×g, 5 minutes).

10) The supernatant was suctioned off. The pelleted cells containing stem cells were recovered.

(II) Preparation Method 2

1) A liquid portion of an aspirate from liposuction was suctioned using a suction tube within a clean bench and was passed through a reservoir with a filter (pore size: 120 µm. The resultant filtrate was enclosed in a closed separation bag.

2) Centrifugation was performed three times using a cell separator (a blood component separating device: ASTEC204 available from AMCO, Inc., Tokyo, Japan) to remove platelets having smaller specific gravity, erythrocytes having larger specific gravity, and granulocytes as much as possible.

3) A fraction (about 30 to 40 ml) containing a high concentration of stem cells was collected. The specific gravity of the isolated cells was within the range of 1.050 to 1.075.

The specific gravity of a cell can be roughly determined as follows. A density gradient centrifugation medium, such as Percoll™, RediGrad™, or the like, was formulated in sodium chloride solution or sucrose solution. Collected cells and density marker beads are added to the mixture, followed by centrifugation. The mixture is separated into 5 to 10 layers, depending on the beads). The layer which contains a cell shows the specific gravity of the cell.

FIG. 1 shows a photograph of the isolated the cells.

Example 3: Characterization of Recovered Stem Cells

The stem cells recovered in Example 2 were characterized by the following procedure using FACS.

About 5 ml of cell suspension was washed twice with staining medium (SM; PBS supplemented with 0.5% bovine serum albumin and 0.05% $NaN_3$). The cells were counted as required.

Labeled antibodies (label(s): phycoerythrin (PE), allophycocyannin (APC), and/or fluorescein isothiocyanate (FITC)) was added to about 1 to $10 \times 10^6$ cells/ml cell suspension to a final concentration of 0.001 to 0.1 µg/ml.

The mixture was incubated on ice for 30 minutes, followed by washing the cells. The concentration of the cell floating solution was adjusted with SM to about $5 \times 10^5$ cells/ml.

FACS Vantage (Becton Dickinson) was used. The label of the antibody was used as a marker to analyze the expression of each CD protein in isolated stem cells. As a result, it was revealed that stem cells, which were derived from a liquid portion of an aspirate from liposuction, expressed CD90 and CD49d as shown in Table 1.

The isolated stem cells were subcultured twice in DMEM. Subculture was conducted at 80% confluence. After the second subculture, the cells were analyzed by FACS as described above. The results are shown in Table 1.

TABLE 1

| (Expression of various CDs in stem cells after two subculture procedures) | |
|---|---|
| CD | Expression level |
| 3 | − |
| 4 | − |
| 11c | − |
| 13 | ++ |
| 14 | − |
| 15 | − |
| 16 | − |
| 19 | − |
| 29 | ++ |
| 31 | + |
| 33 | − |
| 34 | + |
| 36 | ++ |
| 38 | − |
| 44 | + |
| 45 | + |
| 49d | ++ |
| 54 | + |
| 56 | − |

TABLE 1-continued (Expression of various CDs in stem cells after two subculture procedures)

| CD | Expression level |
| --- | --- |
| 58 | + |
| 61 | − |
| 62E | − |
| 62P | − |
| 69 | − |
| 71 | ++ |
| 73 | ++ |
| 90 | ++ |
| 104 | − |
| 105 | ++ |
| 106 | − |
| 117 | + |
| 135 | − |
| 144 | − |
| 146 | + |
| 151 | ++ |
| 235a | − |
| SH3 | + |
| STRO-1 | + |

"−" = no detection of expression, 20% is represented by + & ++.
"+" = detection in 20% or less of cells, and
"++" = detection in 20% or more of cells.

According to the above-described results, although the stem cells prepared from the liquid portion of an aspirate from liposuction included cell populations corresponding to mesenchymal stem cells, the stem cells included CD31 and CD34 positive cells, which are not included in fat-derived stem cells prepared by conventional techniques. Therefore, it can be understood that stem cells prepared by the method of the present invention can be easily and efficiently differentiated into vascular endothelium (vascularization). In addition, CD expression, which was used herein as a marker, was confirmed after two subculture procedures. Therefore, it is understood that the stem cell of the present invention does not substantially change the phenotype after about two subculture procedures.

Example 4: Characterization of Stem Cells Recovered from the Liquid Portion of an Aspirate from Liposuction Obtained from a Plurality of Subjects Further, stem cells were recovered from liquid portions of aspirates from liposuction obtained from a plurality of subjects, followed by characterization. The results are shown below.

TABLE 2

(Results of characterization of stem cells recovered from liquid portions of aspirates from liposuction obtained from a plurality of subjects)

| Subject | A | B | C |
| --- | --- | --- | --- |
| Passage | 7 | 1 | 1 |
| Number of cells | 10,000 | 10,000 | 30,000 |
| Medium | DMEM | M199 | M199 |
| CD4 | − | 5.1 | N.T. |
| CD13 | + | 100.0 | 99.6 |
| CD16 | N.T. | 1.9 | 1.1 |
| CD29 | + | 99.9 | 98.9 |
| CD31 | − | 8.0 | 1.7 |
| CD34 | − | 80.3 | 80.6 |
| CD36 | + | 27.6 | 15.6 |
| CD44 | + | 100.0 | 99.4 |
| CD45 | − | 8.1 | 0.9 |
| CD49d | + | 78.0 | 79.4 |
| CD54 | N.T. | N.T. | 95.6 |
| CD56 | N.T. | 2.1 | 9.0 |
| CD57 | N.T. | N.T. | 0.1 |
| CD69 | − | 0.0 | 0.0 |
| CD71 | + | 95.4 | 53.5 |
| CD73 | N.T. | 89.5 | 98.5 |
| CD90 | + | 100.0 | N.T. |
| CD105 | + | 99.8 | 92.4 |
| CD106 | − | 0.6 | 1.2 |
| CD117 | − | 10.4 | 7.1 |
| CD135 | − | 0.5 | 0.0 |
| CD151 | + | 98.7 | 99.4 |
| CD235a | − | 4.5 | N.T. |
| STRO-1 | N.T. | 4.1 | 5.7 |

Numerals show the proportion (%) of stem cells, which expressed each protein, in a group of cells, "−"=no expression detected, "+"=expression detected, and N.T.=no test.

Most of the collected stem cells were positive for CD13, CD29, CD34, CD36, CD44, CD49d, CD54, CD58, CD71, CD73, CD90, CD105, CD106, CD151, and SH3. Therefore, the adipose-derived precursor cell of the present invention is a cell which expresses at least one protein selected from the group consisting of CD13, CD29, CD34, CD36, CD44, CD49d, CD54, CD58, CD71, CD73, CD90, CD105, CD106, CD151, and SH3. A stem cell expressing CD106 is a feature of the adipose-derived precursor cell used in the present invention. A portion of the stem cell group was positive for CD31, CD45, CD117, and CD146, while another portion was negative.

The stem cell group was negative for CD3, CD4, CD14, CD15, CD16, CD19, CD33, CD38, CD56, CD61, CD62e, CD62p, CD69, CD104, CD135, and CD144. Therefore, the adipose-derived precursor cell of the present invention is a cell which does not express at least one of CD3, CD4, CD14, CD15, CD16, CD19, CD33, CD38, CD56, CD61, CD62e, CD62p, CD69, CD104, CD135, and CD144.

When the stem cell group was cultured in differentiation inducing medium, the expression of proteins specific to an organ, such as bone, cartilage, fat, or the like, was recognized after 2 to 3 weeks. The stem cell group did not express CD56, which is expressed by most fibroblasts, as is different from human dermis-derived cultured fibroblasts. In contrast, the expression of CD105 exhibited by the stem cell group was not usually observed in fibroblasts. The expression of CD49d exhibited by the stem cell group was not typically observed in bone marrow-derived mesenchymal stem cells.

In addition, for CD31, CD34, CD36, CD45, CD106, and CD117, the expression tended to disappear when the period of culture was long. Therefore, if subculture is continued, the expression of CD106 observed before subculture may no longer be observed.

Example 5: Induction of Differentiation of Stem Cells from an Aspirate of Liposuction into Adipocytes Stem cell derived from an aspirate of liposuction were induced into adipocyte differentiation by culturing the stem cells in adipogenic DMEM medium as follows:

An adipogenic DMEM used has the following composition:

| | |
|---|---|
| DMEM (supplemented with 10% FBS) | 100 ml |
| Isobutyl-methyl xanthine (0.5 M) | 100 µl (final conc. 0.5 mM) |
| Dexamethasone ($10^{-4}$ M) | 1 mL (final conc 1 µM) |
| Insulin ($10^{-3}$ M) | 1 mL (final conc 10 µM) |
| Indomethacine | 100 µl (final conc. 200 µM) |

Figure 2:
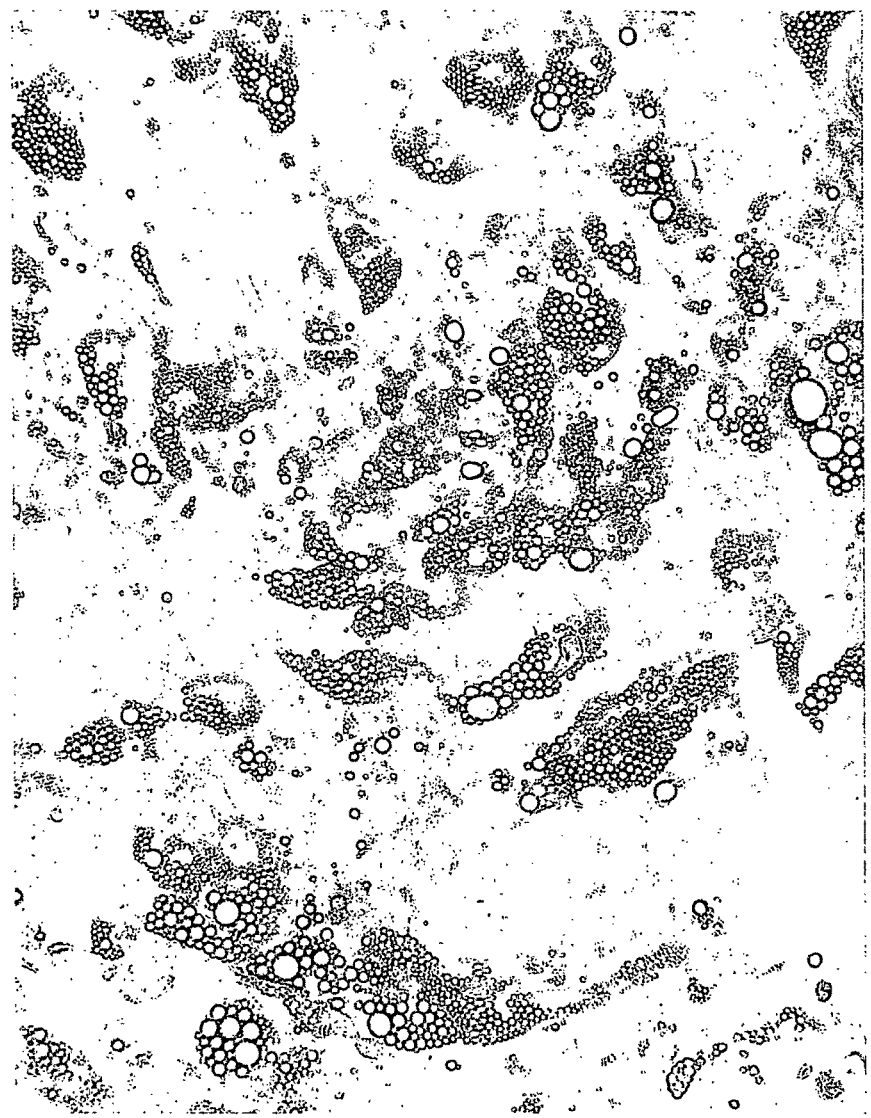
FIG. 2 shows a photograph showing differentiated cells induced by culturing stem cells, which were prepared according to the present invention, in an adipogenic DMEM medium.

About three hundred thousand stem cells as prepared in Example 2 were cultured without passage for about four weeks. As a result, as shown in FIG. 2, stem cells were differentiated into cells containing stored fat-like substances therein.

The differentiated cells were stained with Oil-Red as follows to confirm that the stored fat like substances are fat, and the differentiated cells are actually adipocytes.

Oil-Red O staining was conducted as follows:
1) Discard medium and wash with PBS;
2) Fix the cell with 10% formalin for about 10 minutes;
3) Wash with distilled water;
4) Add 60% isopropyl alcohol for about one minute;
5) Transfer the cells into Oil-Red O staining solution* for 15 minutes;
6) Add 60% isopropyl alcohol for one minute;
7) Wash with distilled water;
8) Add hematoxylin for two minutes to stain nucleus;
9) Wash with distilled water;
10) Add lithium carbonate** for several seconds for coloring;
11) Wash with distilled water.
* Oil-Red O staining solution was prepared as follows:
Oil Red O 0.3 g (SIGMA 0-0625) was solved in 99% isopropyl alcohol 100 ml. In use, this solution and distilled water was mixed at 6:4 ratio and shaken vigorously. Thirty minutes thereafter, the resultant solution was filtered for later use.
** Lithium carbonate was prepared as follows:
3 mg of Lithium carbonate solution (1.54 g in 100 ml distilled water; Sigma-Aldrich) was added to distilled Water 100 ml.

Figure 3:
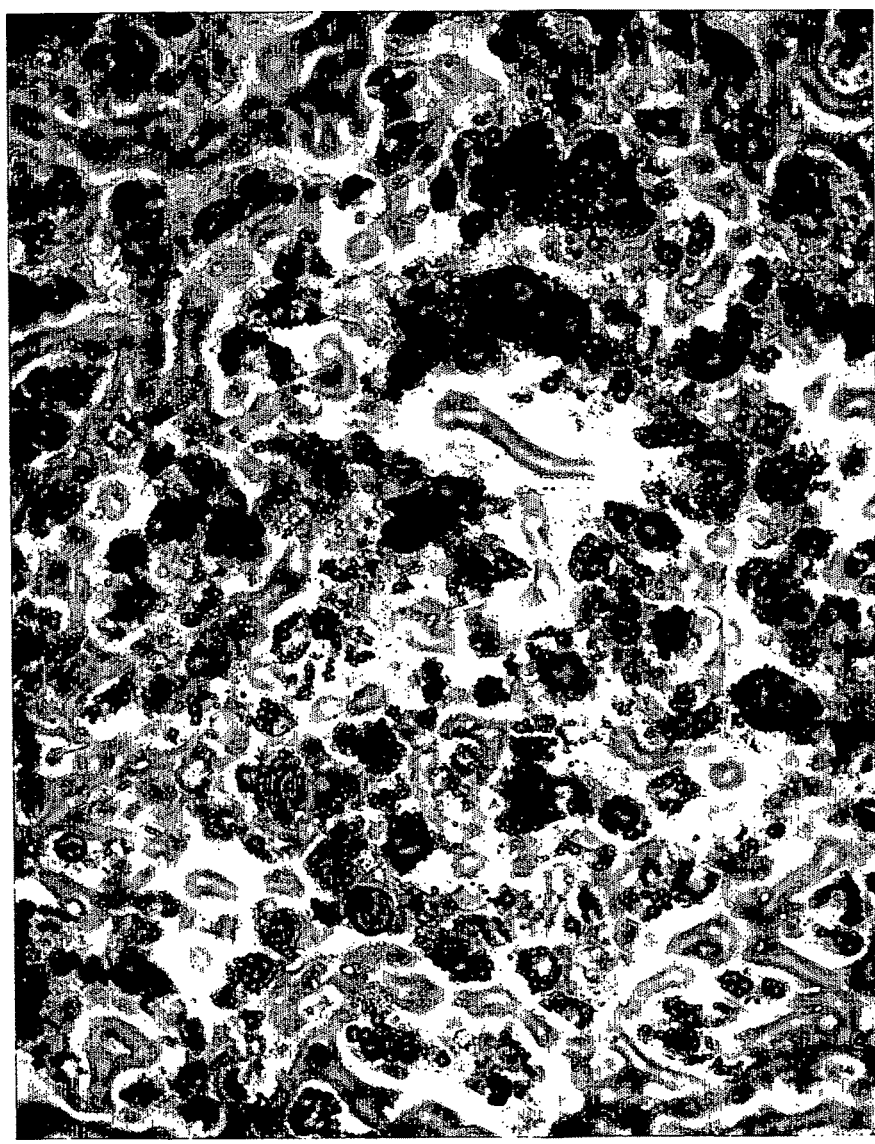
FIG. 3 shows a photograph showing OilRed-O stained differentiated cells induced by culturing stem cells which were prepared according to the present invention, in an adipogenic DMEM medium.

Photographs of stained cells are shown in FIG. 3. As shown in FIG. 3, stem cells prepared in Example 2, are cultured in the above-mentioned adipogenic DMEM to confirm that the substances stored in the cell are fat and therefore the cells differentiated from the stem cells are actually adipocytes.

Example 6: Induction of Differentiation into Cartilage Cells from Stem Cells from an Aspirate of Liposuction Stem cells from an aspirate of liposuction were differentiated into cartilage cells by culturing the stem cells in chondrogenic DMEM medium as follows.

Chondrogenic DMEM medium used herein are prepared as follows:
1) DMEM (no serum added, proper antibiotics are added) 100 mL
Insulin (6.25 mg/mL) 100 µL (added amount: 625 µL);
ascorbate-2-phosphate (5 µM) 1 mL (final conc. 50 nM); and
Fetal bovine serum 1 mL (final conc. 1%) were mixed.
2) The resultant mixture was filtered using 0.22 µm filter, and 1 ml of TGF-β1 (1 µg/ml) was added to the mixture, and stored at 4° C. after pipetting.

Figure 4:
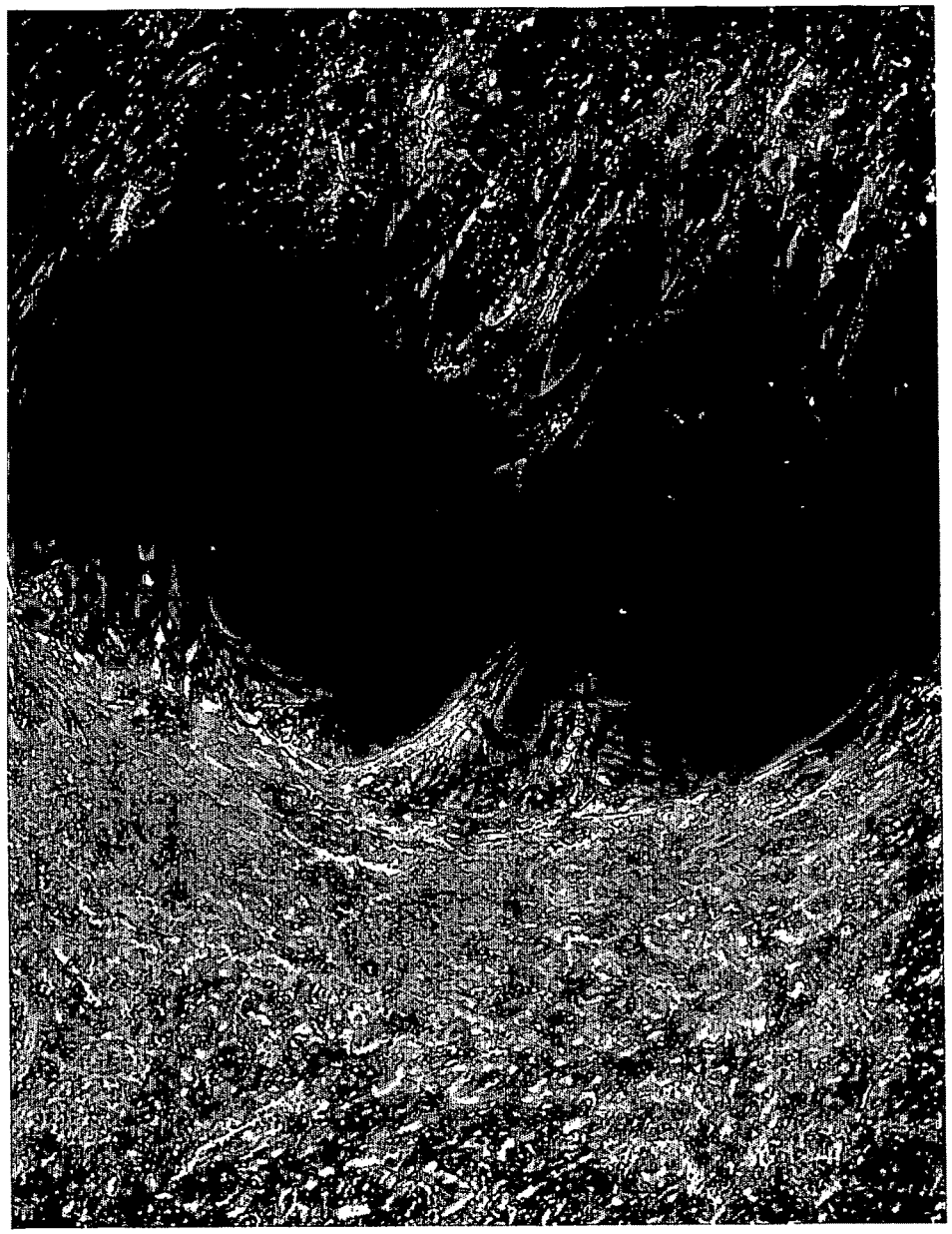
FIG. 4 shows a photograph showing differentiated cells induced by culturing stem cells which were prepared according to the present invention, in a chondrogenic DMEM medium.

About three hundred thousand stem cells as prepared in Example 2 were cultured without passage for about four weeks. As a result, as shown in FIG. 4, stem cells were differentiated into cartilage-like cells forming micro cellular masses.

Differentiated cells were stained by Alcian blue staining to confirm that the differentiated cells are cartilage cells.

Alcian blue staining was conducted as follows:
1) Discard medium and wash with PBS;
2) Fix the cell with 10% formalin for about 10 minutes;
3) Add 3% acetate solution for three minutes;
4) Add Alcian blue staining solution* for about one hour;
5) Add 3% acetate solution for three minutes;
6) Wash with distilled water for two minutes;
7) Add Nuclear Fast Red (Kernechtrot)** for two minutes;
8) Wash with distilled water.
*Alcian Blue 8 GX 1 g was solved in 3% acetate water 100 ml and filtered for later use.
**Nuclear Fast Red solution was prepared as follows:
Nuclear Fast Red (nuclease fast red) 0.1 g was added to 100 ml of distilled water, and aluminum sulfate 5 g was added for boiling solution. The resultant was filtered for later use.

Figure 5:
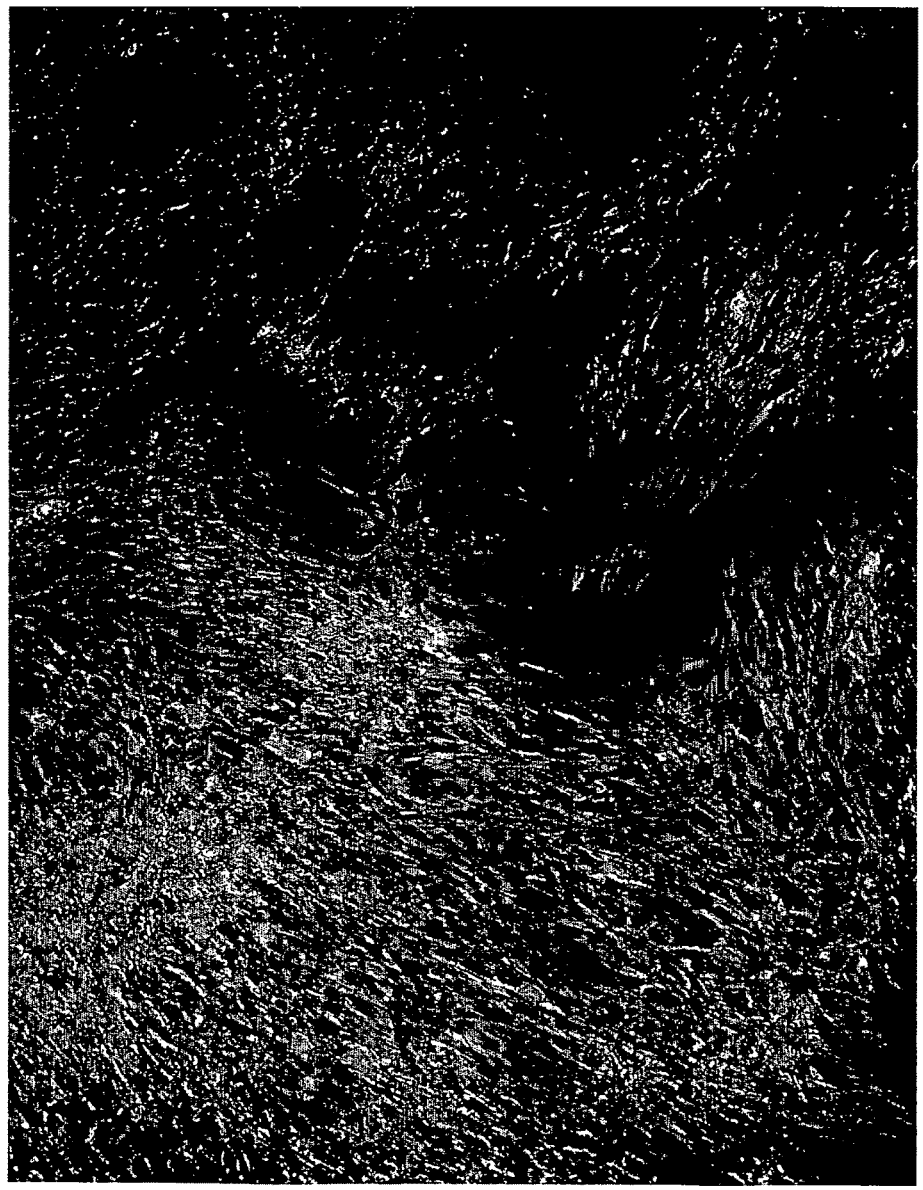
FIG. 5 shows a photograph showing Alcian blue stained differentiated cells induced by culturing stem cells which were prepared according to the present invention, in a chondrogenic DMEM medium.

Photographs of cells stained with Alcian blue are shown in FIG. 5. As shown in FIG. 5, it was confirmed that culturing the stem cells in the above-mentioned chondrogenic DMEM medium were actually cartilage cells.

Example 7: Preparation of Fat Tissue

Next, as differentiated cells, fat tissue was prepared from human subjects who had given their informed consent. Separation was conducted with techniques well known in the art. Briefly, human fat tissue was aseptically separated from fat tissue suctioned from human subjects who had given their informed consent. The tissue mass was preserved in medium for adipocytes ((500 ml) composition=Eagle's medium 4.75 g; 10% $NaHCO_3$ 10 ml; glutamine 0.3 g; kanamycin (20 mg/ml) 1.5 ml; penicillin streptomycin 5 ml; FBS (10%)). The tissue mass may be used as is or may be separated into adipocytes, which are in turn used.

| Ingredients of Eagle's medium (per 9.5 g) | |
|---|---|
| sodium chloride | 6400 mg |
| potassium chloride | 400 mg |
| calcium chloride (anhydride) | 200 mg |
| magnesium sulfate (anyhdride) | 97.7 mg |
| sodium dihydrogen phosphate (anhydride) | 108 mg |
| mercuric nitrate (nonahydrate) | 0.1 mg |
| grape sugar | 1000 mg |
| sodium pyruvate | 110 mg |
| succinic acid | 106 mg |
| sodium succinate (hexahydrate) | 27 mg |
| L-arginine hydrochloride | 84 mg |
| L-cysteine hydrochloride (monohydrate) | 70.3 mg |
| glycine | 30 mg |
| L-histidine hydrochloride (monohydrate) | 42 mg |
| L-isoleucine | 104.8 mg |
| L-leucine | 104.8 mg |
| L-lysine hydrochloride | 146.2 mg |
| L-methionine | 30 mg |
| L-phenylalanine | 66 mg |
| L-serine | 42 mg |
| L-threonine | 95.2 mg |
| L-tryptophan | 16 mg |
| L-disodium tyrosine | 89.5 mg |
| L-valine | 93.6 mg |
| choline bitartrate | 7.2 mg |
| folic acid | 4 mg |

| Ingredients of Eagle's medium (per 9.5 g) | |
|---|---|
| nicotinamide | 4 mg |
| calcium pantothenate | 4 mg |
| pyridoxal hydrochloride | 4 mg |
| riboflavin | 0.4 mg |
| thiamine hydrochloride | 4 mg |
| i-inositol | 7.2 mg |
| phenol red | 5 mg |

Example 8: Mixture of Adipocyte

Next, the adipose-derived precursor cell (PLA) prepared in Example 2 was not subject to further treatment and was mixed with the fat tissue (adipocyte group), which had been prepared as differentiated cells in Example 6. It is determined whether or not differentiation was promoted to cause regeneration.

1 ml (900 mg) of fat tissue mass (A), which had been prepared in Example 6, or a mixture (B) of 1 ml (900 mg) of the fat tissue with 10 ml of suctioned fat-derived stem cells prepared as in Example 2 is subcutaneously injected into the dorsal portion of SCID mice (Charles River, Japan). Injection is performed with a syringe. After 4 weeks, tissue is collected from the injection site. The weight of the implanted fat tissue is determined and the tissue is analyzed. Effects of the mixture of stem cells derived from an aspirate of liposuction on the maintenance of tissue weight can be confirmed.

(Regeneration of Fat Tissue by Mixture of Adipocyte)

When fat-derived stem cells and fat tissue are mixed, the average weight of regenerated fat is heavier than fat tissue alone. Thus, the influence of PLA is clearly demonstrated. When SCID mice are opened for inspection, one can confirm the effects by the regeneration. As seen, the tissue is significantly bigger when the mixture containing fat-derived stem cells is administered.

When only fat tissue is injected, the weight of the fat tissue is reduced to about half after 4 weeks. This may be because the fat tissue underwent necrosis. The reason the weight of the tissue was maintained when the mixture containing fat-derived stem cells are administered, is considered to be that fat-derived stem cells are induced to differentiate into fat tissue, or fat-derived stem cells had a function to prevent disruption of tissue, or both.

Example 9: Effect of PLA which was Maintained and Cultured in DMEM

The stem cell derived from an aspirate from liposuction prepared in Example 2 is maintained in DMEM (the same as used in Example 7). The resultant fat-derived stem cells are used to confirm a similar effect. Specifically, this preparation was used instead of the fat-derived stem cells or adipose-derived precursor cells (PLA) prepared in Example 2 and used in Example 7.

As a result, when 250 million of the fat-derived stem cells are added to 900 mg of fat, about 40 to 50% of the fat tissue successfully grew. Therefore, it is found that stem cells, which are collected and maintained in growth culture, can be used.

Example 10: Effect of Fat-Derived Stem Cells Cultured in M199

Adipose-derived precursor cells cultured in M-199 are used instead of the fat-derived stem cells or adipose-derived precursor cell (PLA) prepared in Example 2 and used in Example 7. M-199 contained the following ingredients.

| Ingredients of M-199 (medium for vascular endothelial cells) (per liter): | |
|---|---|
| Medium 199 | 9.5 g |
| NaHCO$_3$ | 2.2 g |
| FBS | (15%) |
| acidic-FGF | 2 µg |
| heparin | 5 mg |
| antibiotic-antimycotic | 10 ml |
| (Note) the unit of ingredients below is mg/ml | |
| L-alanine | 50 |
| L-arginine•HCl | 70 |
| L-aspartic acid | 60 |
| L-cysteine | 0.1 |
| L-cystine | 20 |
| L-glutainic acid | 150 (H$_2$O) |
| L-glutamine | 100 |
| glycine | 50 |
| L-histidine•HCl•H$_2$O | 20 |
| hydroxy-L-proline | 10 |
| L-isoleucine | 40 |
| L-leucine | 120 |
| L-lysine•HCl | 70 |
| L-methionine | 30 |
| L-phenylalanine | 50 |
| L-proline | 40 |
| L-serine | 50 |
| L-threonine | 60 |
| L-tryptophan | 20 |
| L-tyrosine | 40 |
| L-valine | 50 |
| glutathione (reduced form) | 0.05 |
| CaCl$_2$•2H$_2$O | 264.9 |
| KCl | 400 |
| MgSO$_4$•7H$_2$O | 97.7 (anhydride form) |
| NaCl | 6800 |
| NaHCO$_3$ | 2200 |
| NaH$_2$PO$_4$ | 140 (2H$_2$O) |
| Fe(NO$_3$)$_3$•9H$_2$O | 0.72 |
| CH$_3$COONa•3H$_2$O | 83 |
| phenol red | 15 |
| D-biotin | 0.01 |
| folic acid | 0.01 |
| nicotinamide | 0.025 |
| calcium pantothenate | 0.01 |
| pyridoxal•HCl | 0.025 |
| pyridoxine•HCl | 0.025 |
| riboflavin | 0.01 |
| thiamine•HCl | 0.01 |
| adenine | 10 (SO$_4$) |
| choline chloride | 0.5 |
| hypoxanthine | 0.3 |
| i-inositol | 0.05 |
| p-aminobenzoic acid | 0.05 |
| guanine•HCl | 0.3 |
| xanthine | 0.3 |
| thymine | 0.3 |
| uracil | 0.3 |
| nicotinic acid | 0.025 |
| vitamin A | 0.1 |
| calciferol | 0.1 |
| menadione | 0.01 |
| α-tocopherol | 0.05 |
| ascorbic acid | 20 |
| Tween 80 | 20 |
| cholesterol | 0.2 |
| ATP•2Na | 1 |
| adenylic acid | 0.2 |
| ribose | 0.5 |
| deoxyribose | 0.5 |

As a result, it was found that when adipose-derived precursor cells cultured in M-199 medium are added to fat, fat tissue undergoes growth. Therefore, it was found that stem cells which are maintained in any medium after collection can be used.

Example 11: Application of Bone Cells

Next, bone cells are used to conduct a similar experiment of implanting the cell mixture of the present invention. For bone cells, bones (bone tissue) are collected from mice with techniques well known in the art. The bone tissue is mixed with PLA prepared in Example 2, and the mixture is implanted into a bone. In this case, it is observed that the regeneration of the bone is supported by the mixture implant of the present invention.

Example 12: Application to Vascularization

Next, blood vessel cells are used to conduct a similar experiment of implanting the cell mixture of the present invention. For blood vessel cells, blood vessels (blood vessel tissue) are collected from mice with techniques well known in the art. The blood vessel tissue is mixed with PLA prepared in Example 1, and the mixture is implanted into a blood vessel. In this case, it is observed that the regeneration of the blood vessel is supported by the mixture implant of the present invention.

Example 13: Assay of Preparation Conditions for Stem Cells

The condition of density gradient centrifugation of cell layers used in (Example 2: Preparation of stem cell suspension from an aspirate of liposuction), (I) Preparation method 1, was 400×g, for 30 minutes using Ficoll. Next, the conditions of such density gradient centrifugation were further assayed in detail.

(1) Study of Media Used

Media used for density gradient centrifugation usable except for Ficoll, include Percoll (R), Histopaque (R), and Lymphoprep and the like. These media were used for density gradient centrifugation of cell layers and compare the results with those of Ficoll. Isolated cells are measured using FACS. Medium presenting the best purity is Ficoll.

(2) Study of Centrifugation Condition

In Example 2, centrifugation at 400×g, for thirty minutes were conducted. Next, the following centrifugation conditions were studied.

200×g for sixty minutes, 400×g for twenty minutes 400×g for thirty minutes, 400×g for forty minutes, 600×g, for thirty minutes, and 800×g, for twenty minutes, were tested using Ficoll as medium for isolating stem cells. Purity of cells was analyzed with FACS. 400×g, for thirty minutes presented the purest and highest yield for isolating stem cells.

Example 14: Preparation of Stem Cells from Material of Liposuction

Next, in order to examine whether material of liposuction before separating into aspirates and tissues (hereinafter also called as "fat tissue+aspirate"), we conducted a similar separation experiment with materials of liposuction before separation.

The method for such a separation was as follows:
1. A vessel with a cover containing "fat tissue+aspirate" (Fat tissue was overlaid upon an "aspirate") was added a collagenase (7.5% collagenase, Sigma, a 1/100 volume of the total sample was added) and was shaken at an appropriate speed. After shaking at 37° C. for thirty minutes, collagenase, a major component of inter-adipocyte matrices, was degraded to facilitating isolation of adipocytes. Here eight 500-ml tubes or four 1000-ml tubes were used.
2. The resultant sample was subjected to centrifugation at 800×g, thereby separating fat components and cells, which fat components have less specific gravity than cells. After centrifugation, the materials were separated into four layers including oil layer, substrate layer, liquid layer, and cell layer.
3. The oil layer, substrate layer, and liquid layer were aspirated to obtain the cell layer only. The cell layer was optionally filtered using filters with 500 μm, and 250 μm. It appears that 500 μm-filter is not necessary.
4. Add 10 ml lysis buffer (for example, ammonium chloride and potassium bicarbonate aqueous solution), and agitate for 2-5 minutes to lyse erythrocytes. Optionally, this lysis step can be omitted.
5. Phosphate buffered saline was added to the resultant pellet. The lysis buffer reaction was terminated. The lysed sample was filtered with 100-μm filter. 175 ml-conical tubes were used for centrifugation.
6. The resultant sample was subjected to further centrifugation at 800×g or 400×g for five minutes. Pelleted cells are the cells of interest.
7. Aspirate supernatant to remove unnecessary solution and a concentration of the cells was attained Collected cells were subjected to similar analyses.

Example 15: Stem Cells from "Fat Tissue+Aspirate

For the stem cells as prepared according to Example 14 were analyzed as in Example 4.

Most of the collected stem cells from "fat tissue+aspirate" were positive for CD13, CD29, CD34, CD36, CD44, CD49d, CD54, CD58, CD71, CD73, CD90, CD105, CD106, CD151, and SH3. Therefore, the adipose-derived precursor cell of the present invention is a cell which expresses at least one protein selected from the group consisting of CD13, CD29, CD34, CD36, CD44, CD49d, CD54, CD58, CD71, CD73, CD90, CD105, CD106, CD151, and SH3. A stem cell expressing CD106 is a feature of the adipose-derived precursor cell used in the present invention. A portion of the stem cell group was positive to CD31, CD45, CD117, and CD146, while another portion was negative.

The stem cell group from "fat tissue+aspirate" stem cells was negative for CD3, CD4, CD14, CD15, CD16, CD19, CD33, CD38, CD56, CD61, CD62e, CD62p, CD69, CD104, CD135, and CD144. Therefore, the adipose-derived precursor cell of the present invention is a cell which does not express at least one of CD3, CD4, CD14, CD15, CD16, CD19, CD33, CD38, CD56, CD61, CD62e, CD62p, CD69, CD104, CD135, and CD144.

When the stem cell group from "fat tissue+aspirate" cells was cultured in differentiation inducing medium, the expression of proteins specific to an organ, such as bone, cartilage, fat, or the like, was recognized after 2 to 3 weeks. The stem cell group did not express CD56, which is expressed by most fibroblasts, and is different from human dermis-derived cultured fibroblasts. In contrast, the expression of CD105 exhibited by the stem cell group was not usually observed in fibroblasts. The expression of CD49d exhibited by the stem cell group was not typically observed in bone marrow-derived mesenchymal stem cells.

In addition, for CD31, CD34, CD36, CD45, CD106, and CD117, the expression tended to disappear when the period of culture was long. Therefore, if subculture is continued, the expression of CD106 observed before subculture may not be observed.

As such even if using "fat tissue+aspirate" as a source for stem cells, stem cells with good qualities were obtained. Therefore, it is demonstrated that separation or isolation of fat tissue (adipose) is not necessary for obtaining stem cells from liposuction materials. Further, a large amount of stem cells can be obtained from the material.

Example 16: Growth of the Stem Cells of the Present Invention

Next, an aspirate of liposuction was processed as in Example 2 (Preparation methods 1) except for omitting removal of erythrocytes to obtain stem cells.

$1.8 \times 10^7$ cells of the prepared stem cells were cultured on a 60-mm dish with M199 (using a gelatin coated dish) and DMEM (using a non-coated dish) as a culture medium Counting the number of the cells was started on Day 6 (or Day 3 for Round 2) and cell number count was conducted every other day.

The results are as follows:

| Round 1 | | | | | |
|---|---|---|---|---|---|
| Day | 6 | 8 | 10 | 12 | 14 |
| medium M199 | 1.90E+04 | 7.80E+04 | 4.15E+05 | 4.65E+05 | 3.85E+05 |
| medium DMEM | 8.50E+03 | 2.60E+04 | 7.20E+04 | 1.19E+05 | 1.26E+05 |

| Round 2 | | | | | |
|---|---|---|---|---|---|
| Day | 3 | 5 | 7 | 9 | 11 |
| medium M199 | 3.90E+04 | 1.75E+05 | 3.17E+05 | 3.40E+05 | 4.50E+05 |
| medium DMEM | 3.50E+04 | 9.30E+04 | 1.90E+05 | 2.09E+05 | 2.80E+05 |

Figure 6:
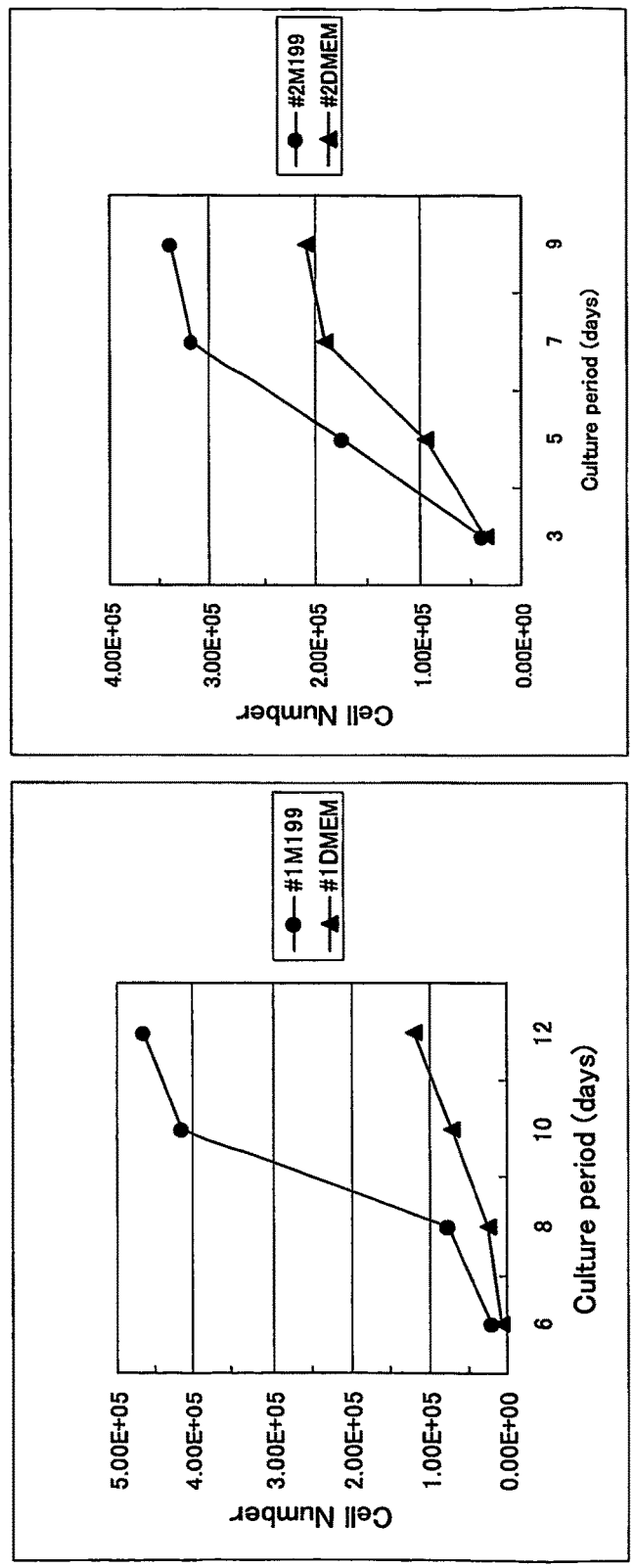
FIG. 6 shows a growth curve of stem cells prepared from material from liposuction without erythrocyte removal.
Figure 7:
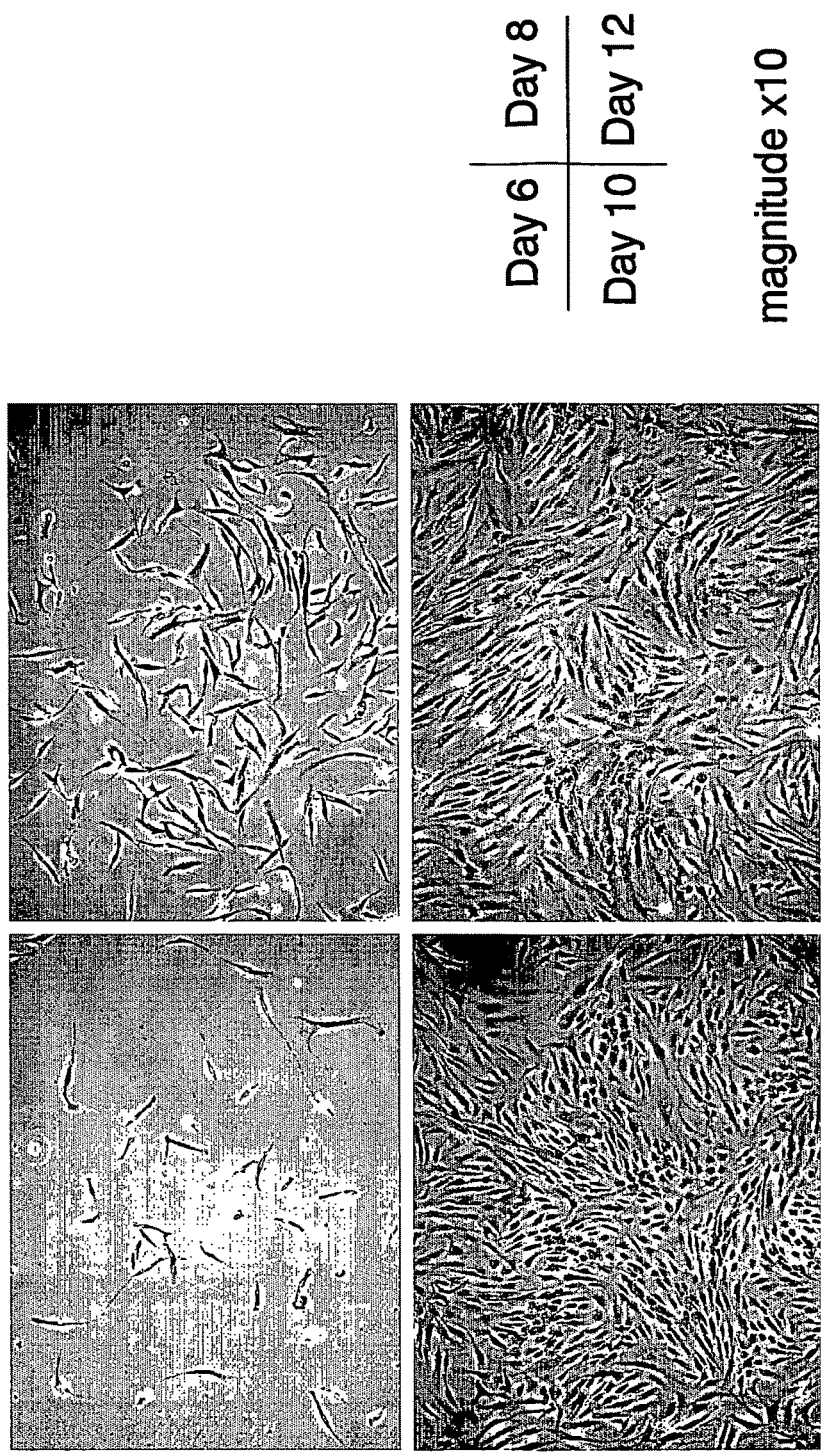
FIGS. 7-10 show photographs showing growth of stem cells prepared from material from liposuction without erythrocyte removal, in DMEM medium (FIG. 7=Round 1; Days 6, 8, 10 and 12.
Figure 8:
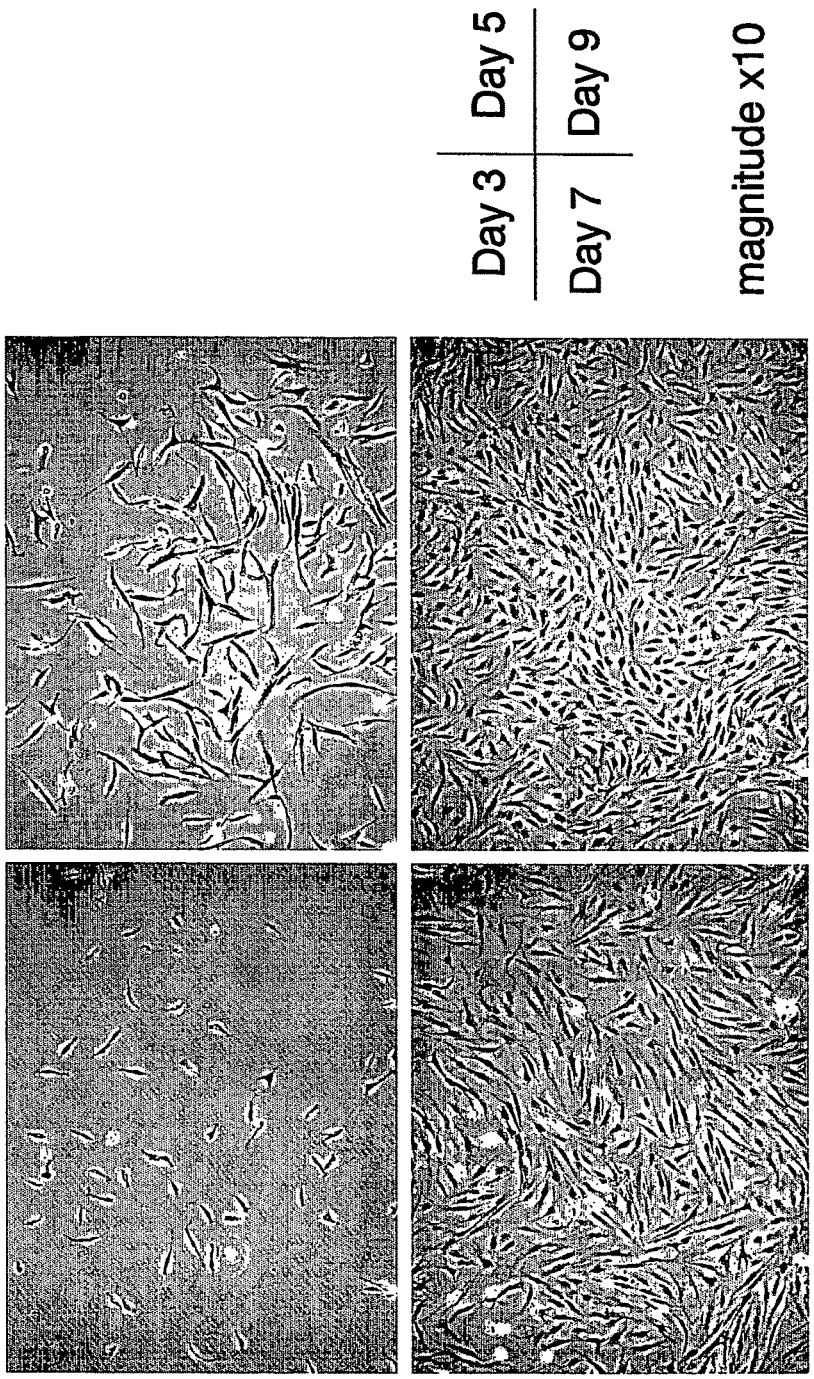
Figure 9:
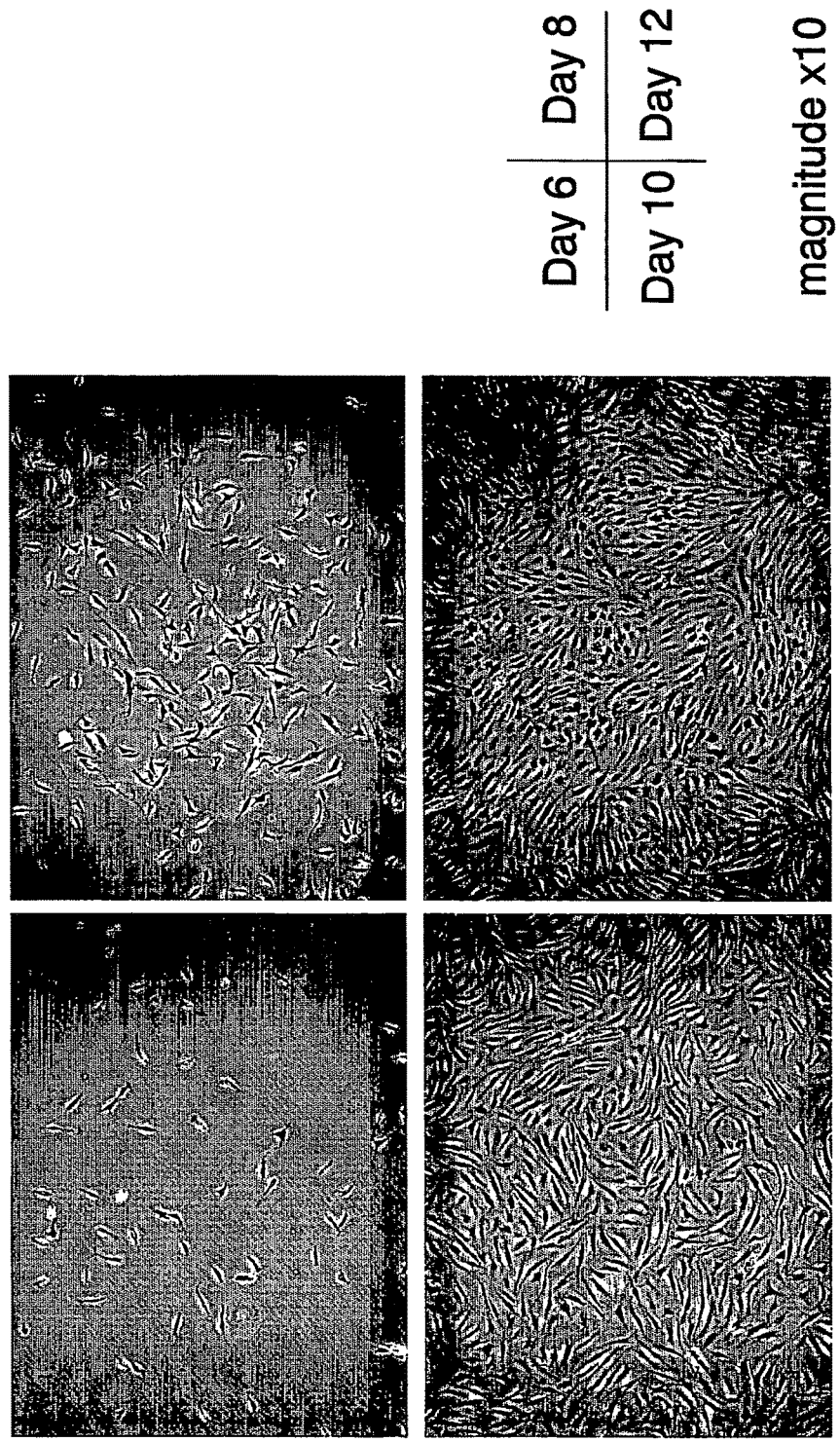
Figure 10:
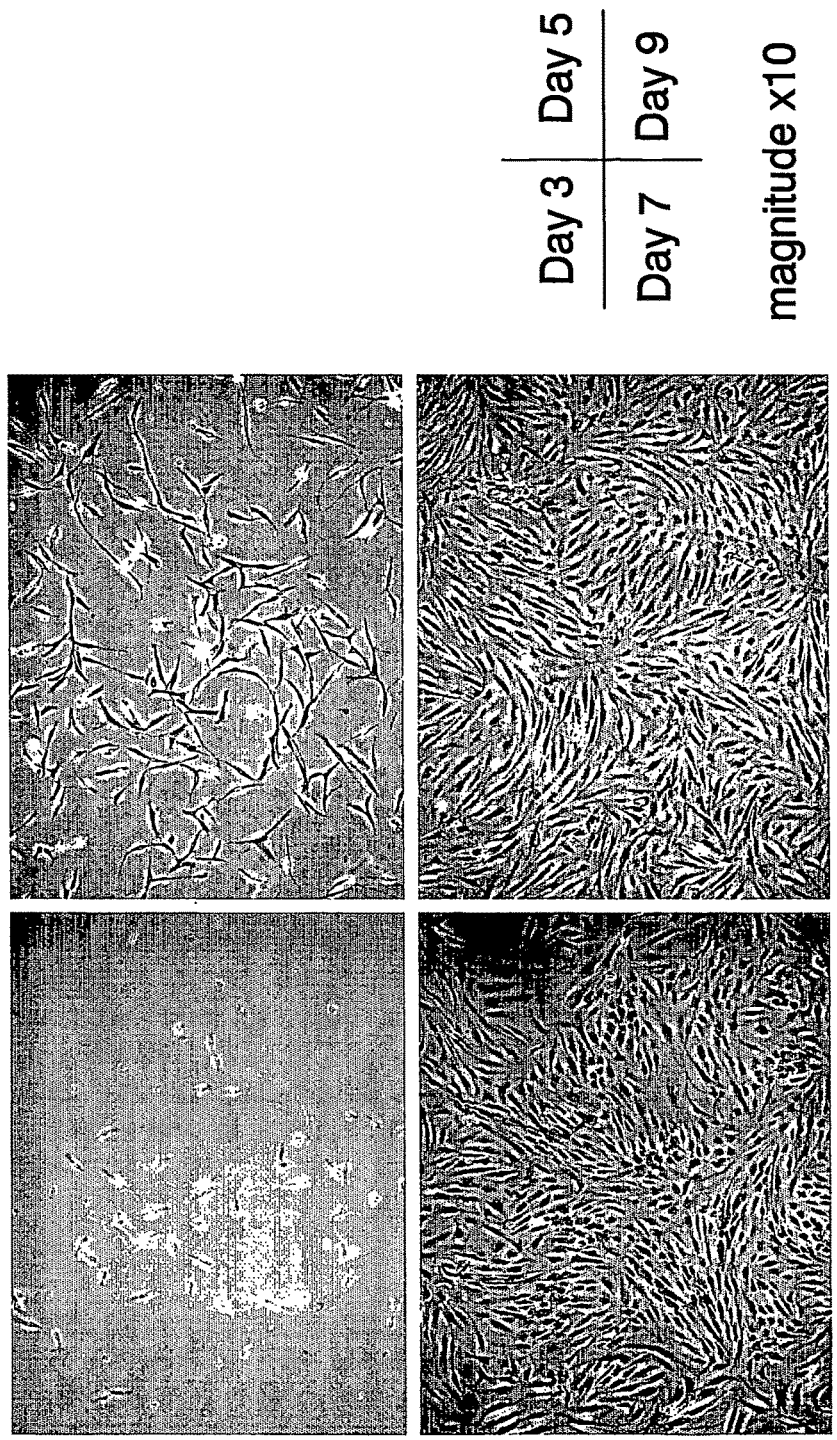
Figure 11:
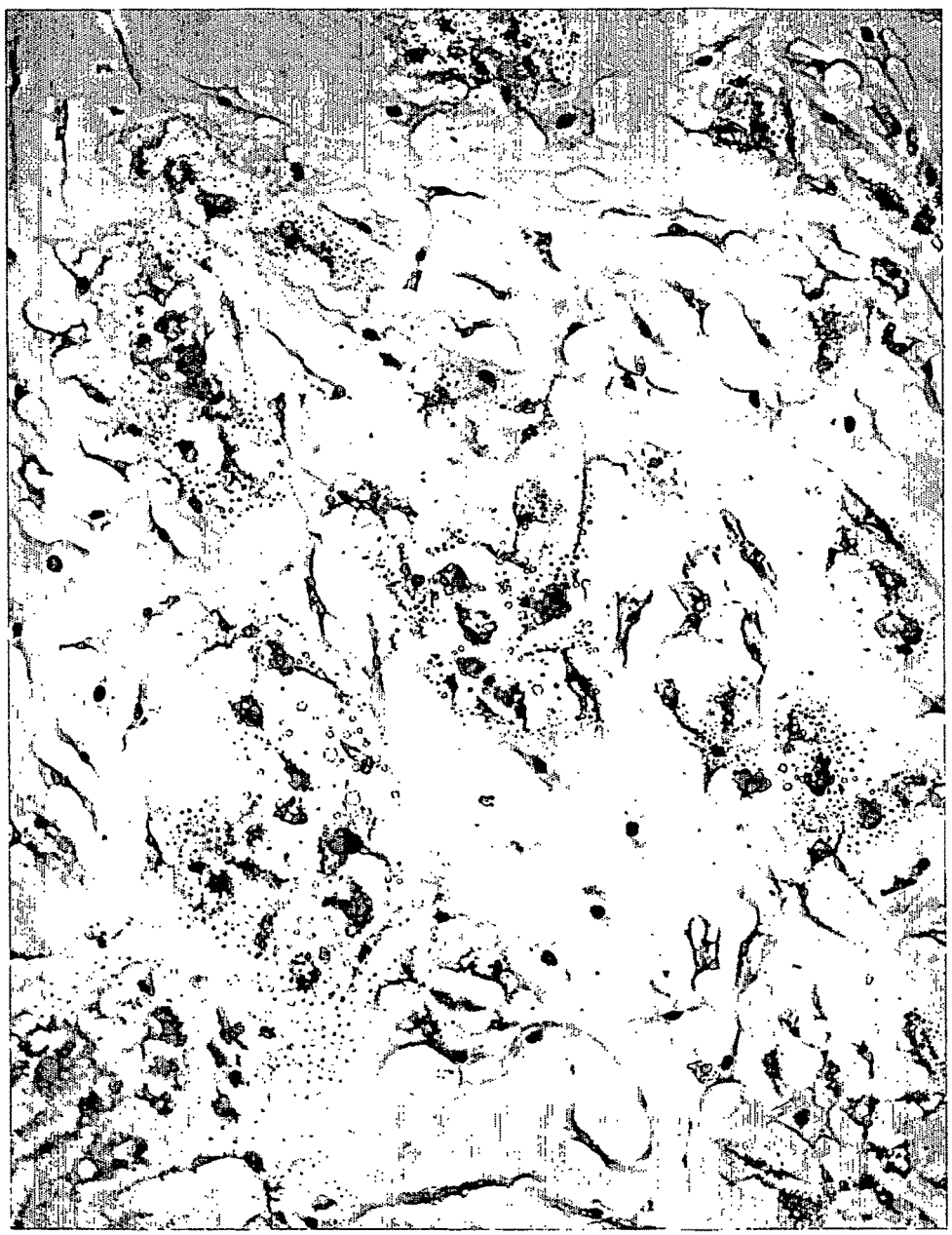
FIGS. 11-26 show photographs under a variety of culture conditions. The following table lists the condition, days of culture, magnitude induction/control and culture/seed. In the right-most column, the term "induction" refers to that cells are subjected to differentiation conditions, the term "control" refers to that cells are subjected to non-differentiation conditions. In the fifth column, the term "culture" refers to the condition where ten days culture after seeding was conducted before the induction started, whereas the term "seed" refers to the condition where no culture was conducted before the induction started.
Figure 12:
Figure 13:
Figure 14:
Figure 15:
Figure 16:
Figure 17:
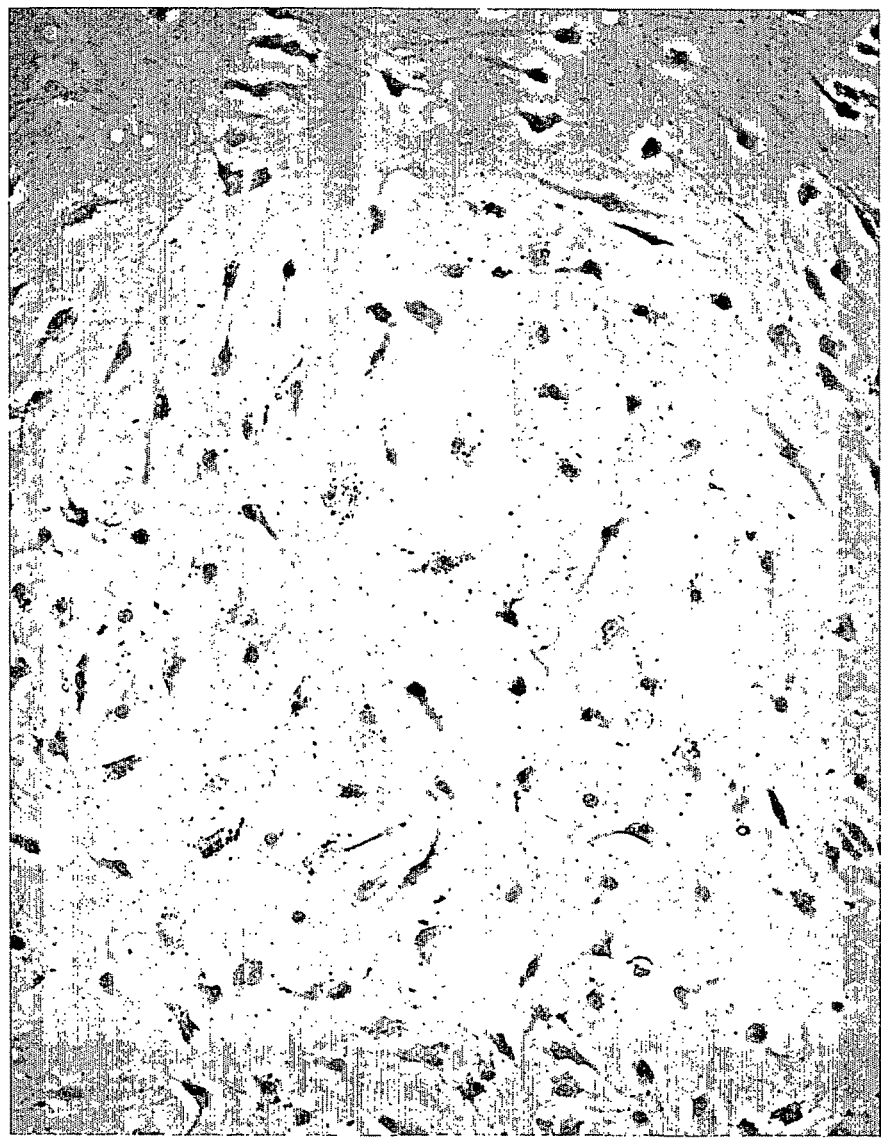
Figure 18:
Figure 19:
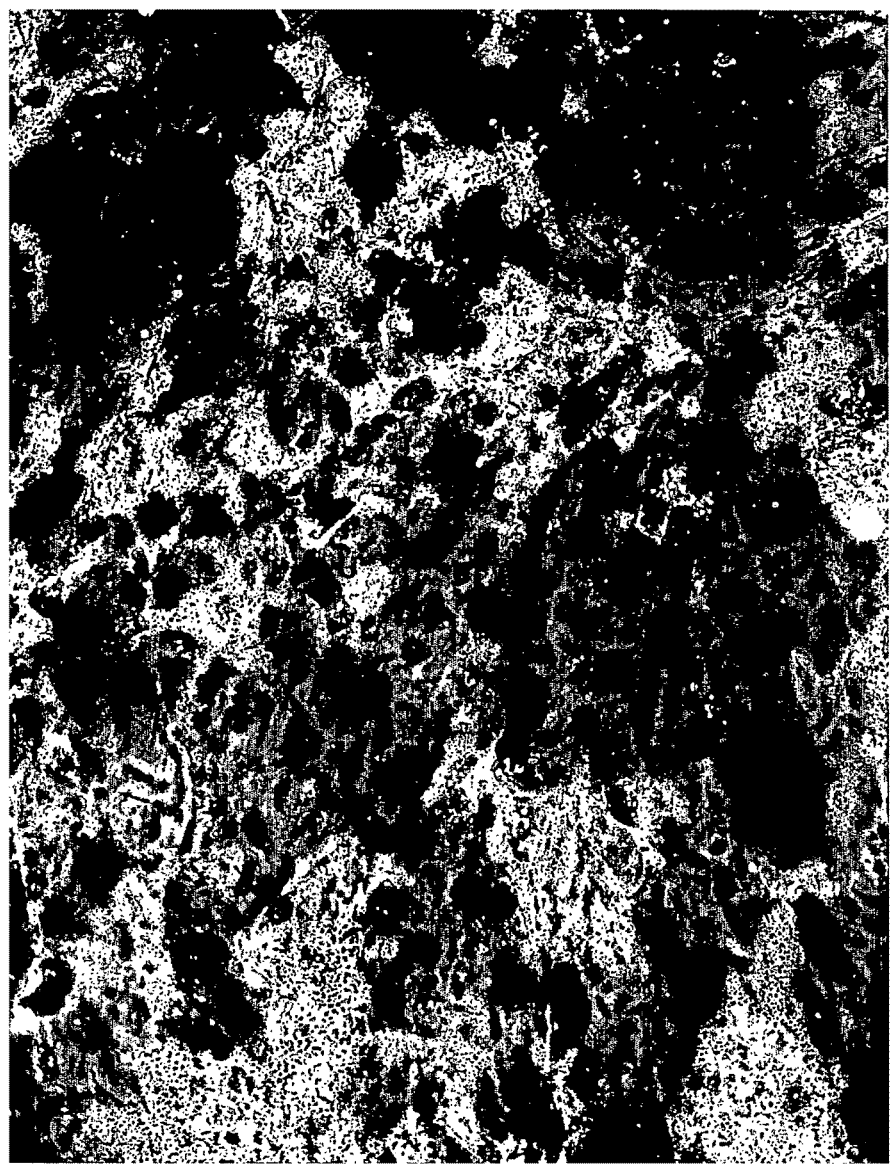
Figure 20:
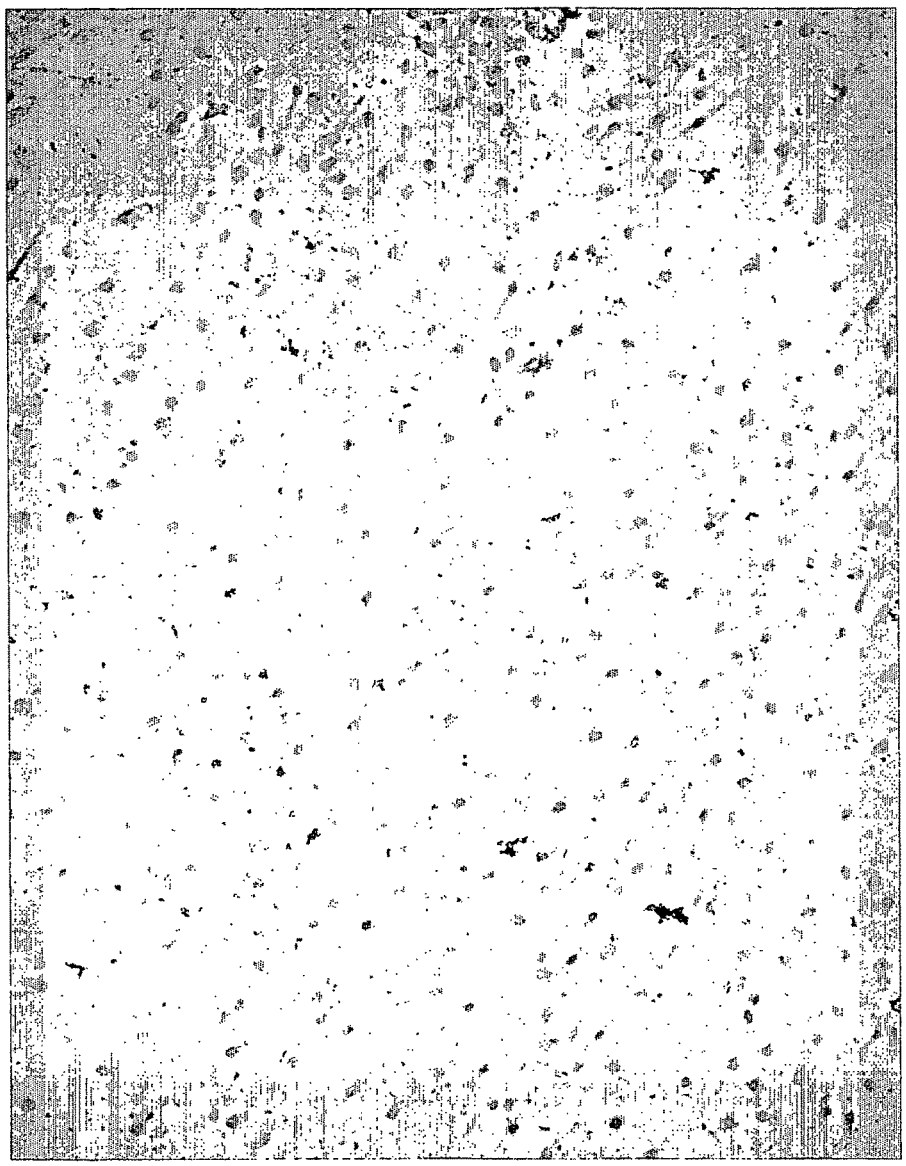
Figure 21:
Figure 22:
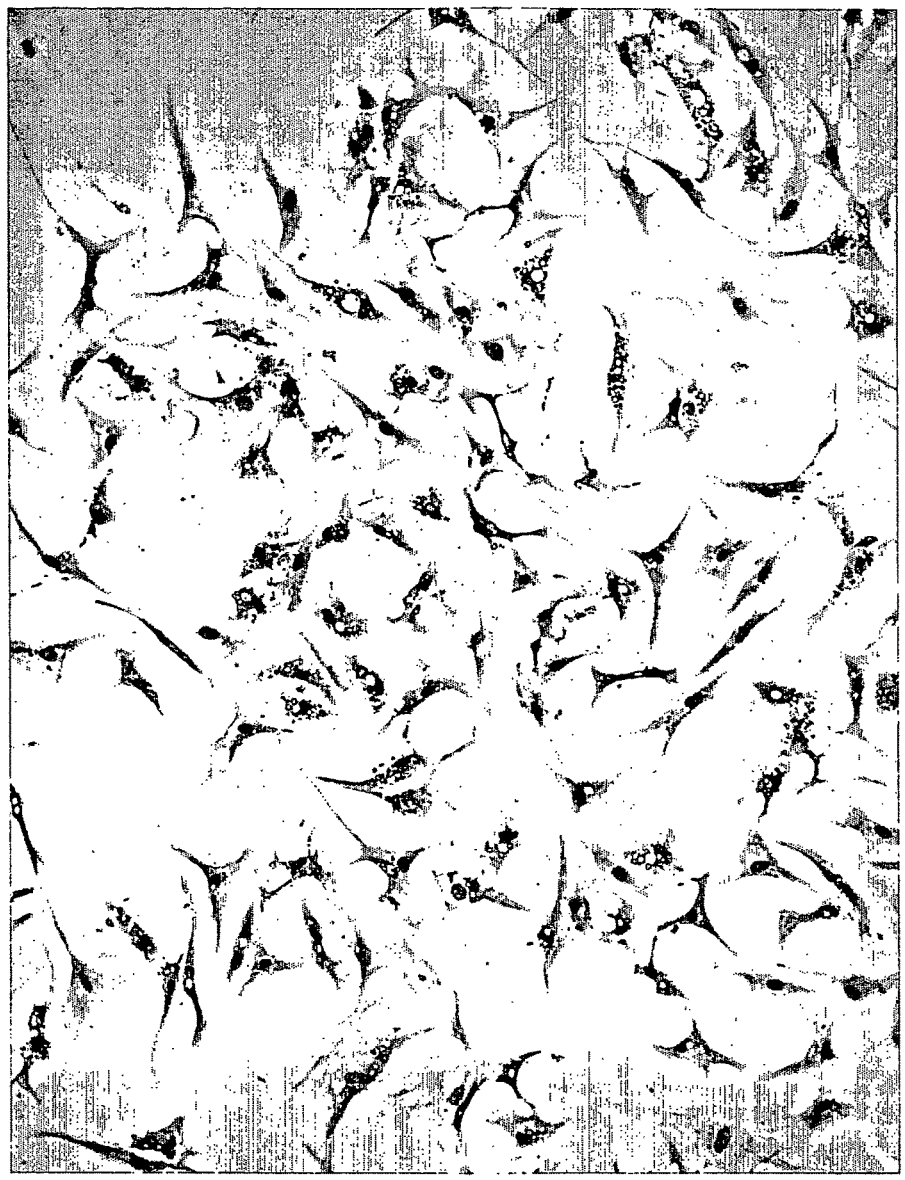
Figure 23:
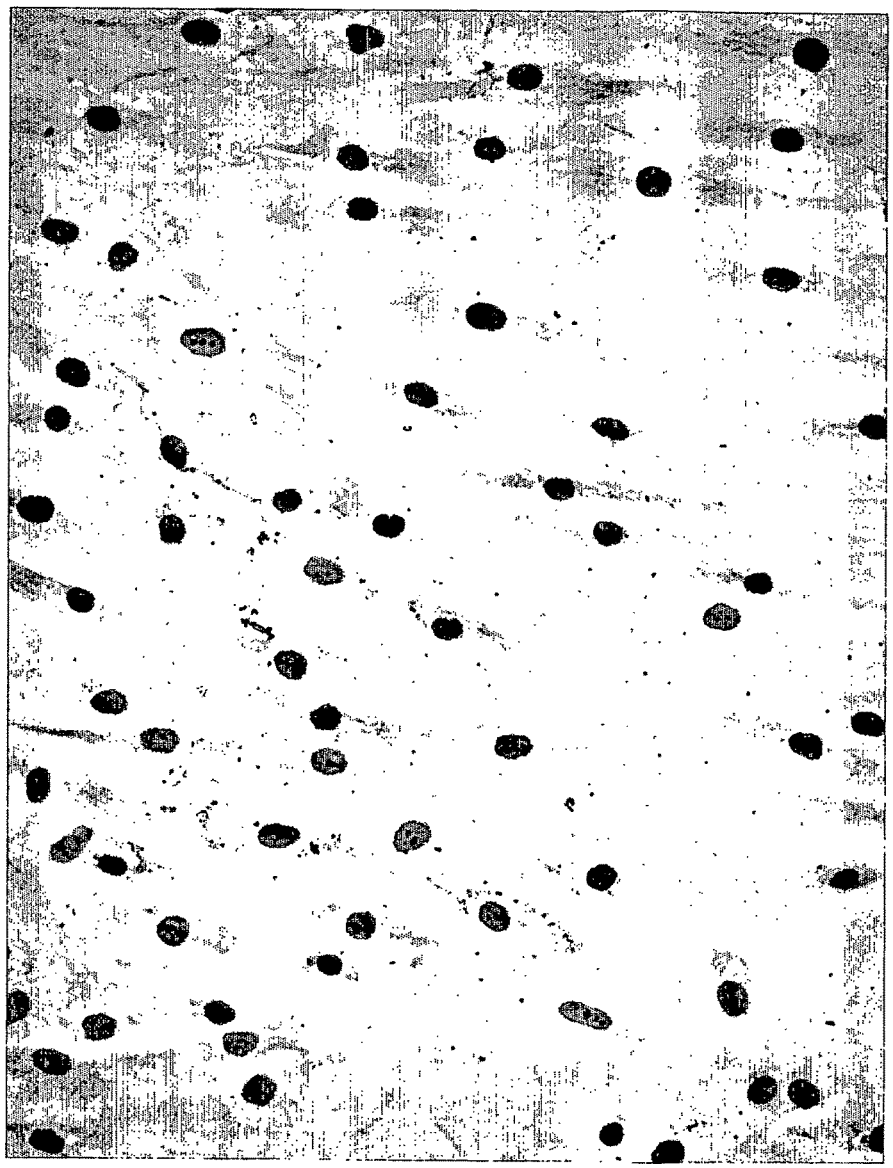
Figure 24:
Figure 25:
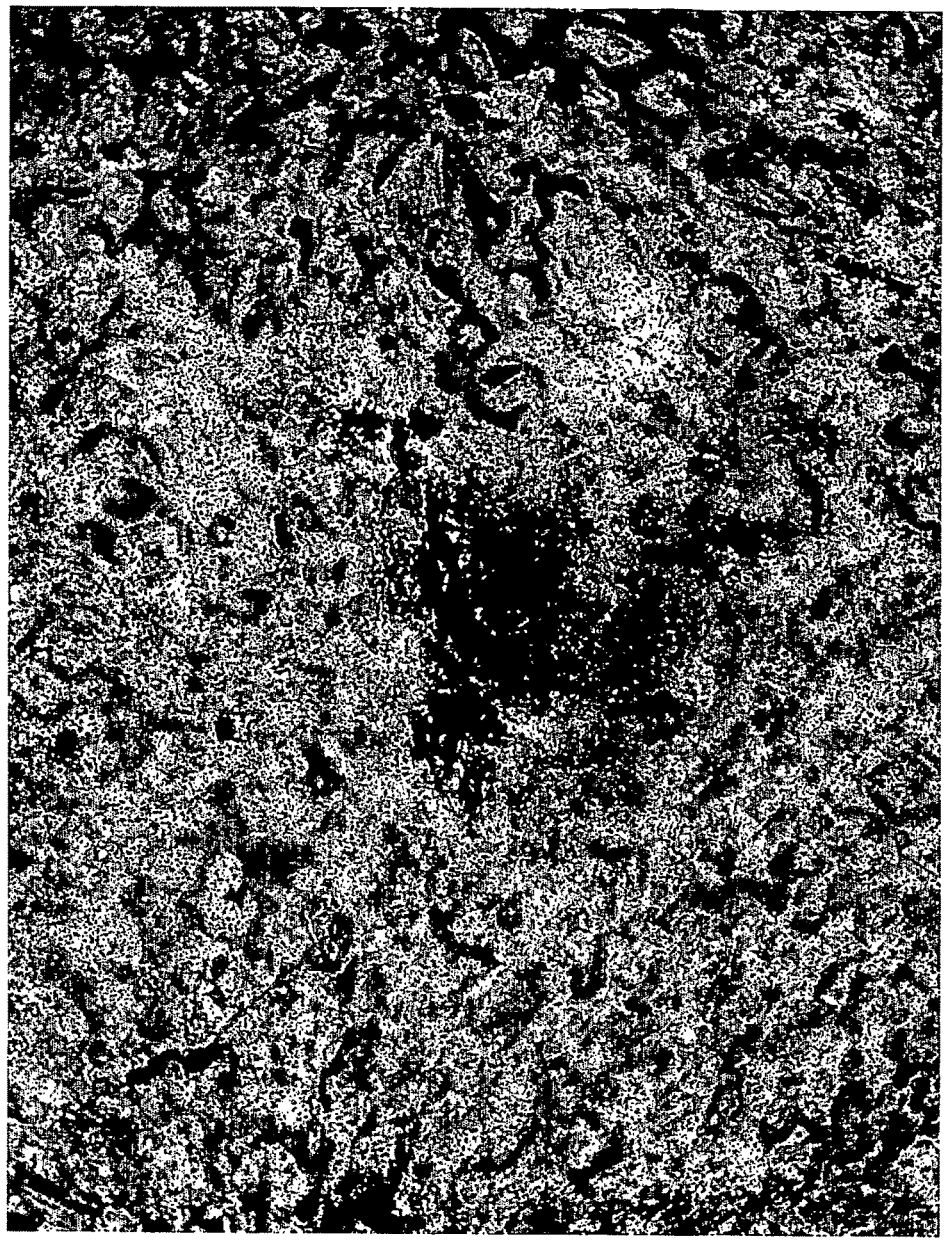
Figure 26:
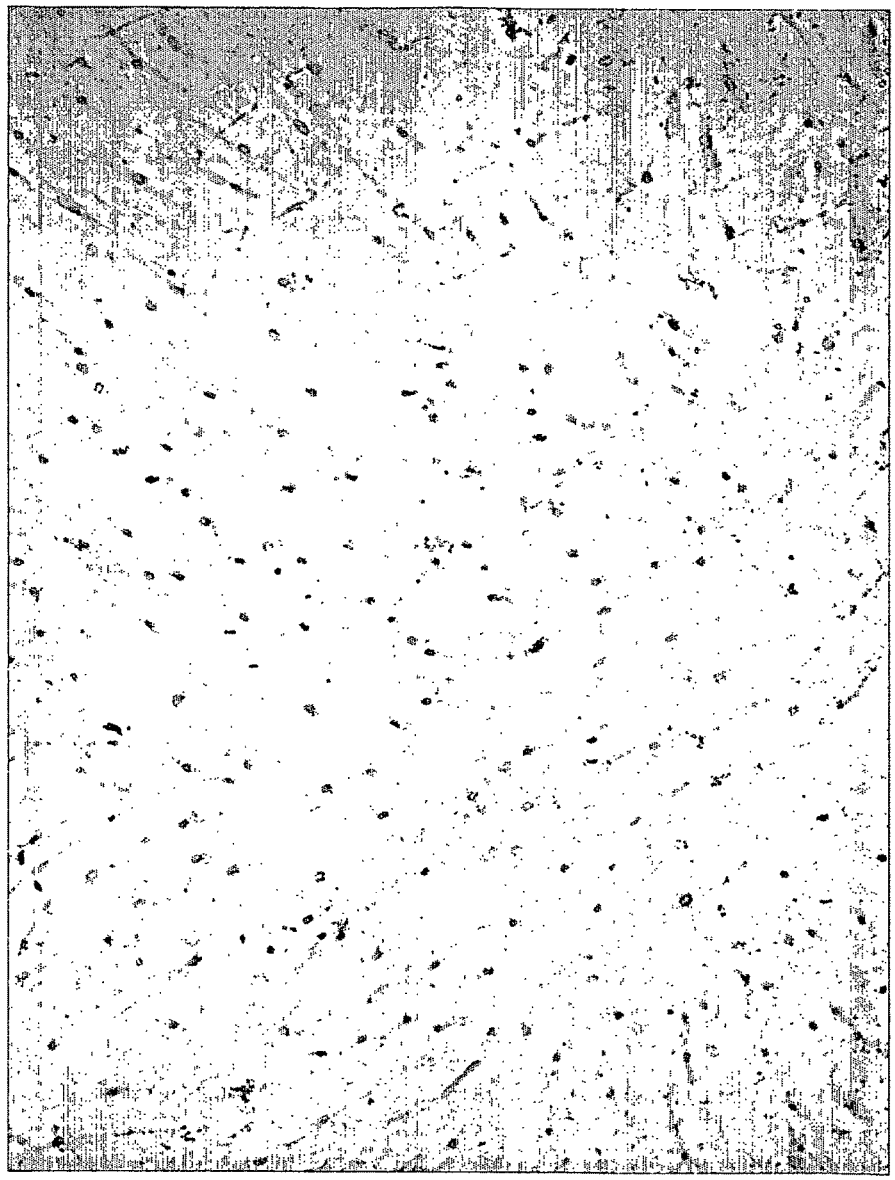

As can be seen from the above Table, it was shown that the erythrocyte removal is not necessary for obtaining stem cells in an efficient manner, since the growth curve is similar to the stem cells prepared from an aspirate of liposuction. Growth curves are also shown in FIG. 6. FIGS. 7-10 show photographs showing growth of stem cells prepared from material from liposuction without erythrocyte removal, in DMEM medium (FIG. 7=Round 1; Days 6, 8, 10 and 12; and FIG. 8=Round 2; Days 3, 5, 7 and 9) and M199 medium (FIG. 9=Round 1; Days 6, 8, 10 and 12; and FIG. 10=Round 2; Days 3, 5, 7 and 9).

Example 17: Assay of Growth with Sub-Confluent Conditions

In this example, it was demonstrated that culture under sub-confluent conditions results in induction of differentiation into a variety of differentiated cells.

The protocols used are as follows:
1) Differentiation into Bone

Collected cells were cultured on a 60-mm dish at a concentration of $1.8 \times 10^7$ cells/dish in DMEM medium. After ten days culture, the cells became subconfluent, and at that time a differentiation induction medium (composition: exemplary osteogenesis medium may be DMEM supplemented with 10% FBS and 5% horse serum, containing 1 µM dexamethasone, 50 µM ascorbate-2-phosphate, 10 mM β-glycerophosphate, and 1% ABAM) was replaced with the existing medium and cultured for twenty two days. The cells were observed using von Kossa staining.

Von Kossa Staining:

Culture medium is discarded and a sample of interest is washed with phosphate buffered saline (PBS). Fix the washed sample with 4% paraformaldehyde for ten minutes. The sample is washed with milliQ water. The sample is contacted with 2.5% silver nitrate for twenty minutes under dark. The sample is washed with milliQ water. Place the sample under fluorescent lamp for fifteen minutes. The sample is incubated with 0.5% hydroquinone for two minutes, and subsequently incubated with 5% sodium thiosulfate for two minutes. The sample is then washed with milliQ water. The sample is stained with Nuclear Fast Red for two minutes. The sample is then washed with milliQ water. The sample is mounted with MountQuick (Daido Sangyo, Japan), and observed under a microscope.

2) Differentiation into Cartilage

Collected cells were cultured on a 60-mm dish at a concentration of $1.8 \times 10^7$ cells/dish in DMEM medium. After ten days culture, the cells became subconfluent, and at that time a differentiation induction medium (composition: exemplary chondrogenesis medium may be DMEM supplemented with 1% FBS, containing 6.25 µg/ml insulin, 6.25 µg/mL transferrin, 10 ng/ml TGF β1, 50 nM ascorbate-2-phosphate, and 1% ABAM) was replaced with the existing medium and cultured for twenty two days. The cells were observed using Alcian blue staining.

Alcian Blue Staining:

Medium is discarded from a sample of interest. The sample is fixed with 4% paraformaldehydef for ten minutes. The sample is washed with milliQ water. The sample is washed with 3% acetate for three minutes. The sample is soaked in Alcian blue staining solution (composition: exemplary adipogenesis medium may be DMEM supplemented with 10% FBS, containing 0.5 mM IBMX, 1 µM dexamethasone, 10 µM insulin, 200 µM indomethacine, and 1% AMAM.) for thirty minutes. The sample is washed with 3% acetate for three minutes. The sample is washed with milliQ water. The sample is then stained with Nuclear Fast Red for two minutes. The sample is then washed with milliQ water. The sample is mounted with MountQuick (Daido Sangyo, Japan), and observed under a microscope.

3) Differentiation into Fat

Collected cells were cultured on a 60-mm dish at a concentration of $1.8 \times 10^7$ cells/dish in DMEM medium. After ten days culture, the cells became sub-confluent, and at that time a differentiation induction medium (composition: exemplary adipogenesis medium may be DMEM supplemented with 10% FBS, containing 0.5 mM IBMX, 1 µM dexamethasone, 10 µM insulin, 200 µM indomethacine, and 1% AMAM.) was replaced with the existing medium and cultured for twelve days. The cells were observed using Oil-Red-O staining.

Oil Red-O Staining:

Culture medium is discarded and a sample of interest is washed with phosphate buffered saline (PBS). Fix the washed sample with 4% paraformaldehyde (PFA) for ten minutes. The sample is washed with milliQ water. The sample is soaked in 60% isopropyl alcohol for one minute. The sample is washed with milliQ water. The sample is soaked with hematoxylin for ten minutes. The sample is washed with milliQ water. The sample is then soaked with lithium carbonate for a couple of seconds, and then washed with milliQ water. The sample is mounted with MountQuick (Daido Sangyo, Japan), and observed under a microscope.

1) Oil-Red O staining solution was prepared as follows:
Oil-Red O 0.3 g is dissolved into 99% 100 ml of isopropyl alcohol. At use, this solution was mixed with milliQ water at the ratio of 6:4, and agitate for let stand for thirty minutes. The mixed solution was filtered before use.

2) Lithium Carbonate Solution:
Three ml of lithium carbonate saturated solution (1.54 g of lithium carbonate per 100 ml) was added to 100 ml of milliQ water.

The results are shown in FIGS. 11-20. As can be seen, the stem cells as prepared in Example 3 or 15 showed good quality of pluripotency.

Example 18: Assay of Growth with Sub-Confluent Conditions—without Erythrocyte Removal Step In this example, it was demonstrated that culture under sub-confluent conditions results in induction of differentiation into a variety of differentiated cells, even if the raw materials were prepared without erythrocyte removal step.

The differentiation steps used are the same as in Example 17.

Similar results were obtained as in Example 17. As a result, the stem cells as prepared without erythrocyte removal step, showed good quality of pluripotency.

Example 19: Differentiation with Differentiation Media

In this example, it was demonstrated that culture using differentiation media, results in induction of differentiation into a variety of differentiated cells.

The protocols used are as follows:
1) Differentiation into Bone

Collected cells are seeded on a 60-mm dish at a concentration of $1.8 \times 10^7$ cells/dish in a differentiation induction medium (composition: exemplary osteogenesis medium may be DMEM supplemented with 10% FBS and 5% horse serum, containing 1 μM dexamethasone, 50 μM ascorbate-2-phosphate, 10 mM β-glycerophosphate, and 1% ABAM). After twenty-two days of culture, the samples were evaluated with von Kossa staining. Von Kossa staining was conducted as described above in Example 17.

2) Differentiation into Fat

Collected cells were seeded on a 60-mm dish at a concentration of $1.8 \times 10^7$ cells in a differentiation induction medium (composition: exemplary adipogenesis medium may be DMEM supplemented with 10% FBS, containing 0.5 mM IBMX, 1 μM dexamethasone, 10 μM insulin, 200 μM indomethacine, and 1% AMAM). After twenty-five days of culture, the samples were evaluated using Oil Red-O staining. Oil Red-O staining was conducted as described above in Example 17.

The results are shown in FIGS. 21-26. As can be seen, the stem cells as prepared in Example 3 or 15 showed good quality of pluripotency using a differentiation induction medium after no culture into sub-confluent state.

Example 20: Assay of Growth with Differentiation Induction Media—without Erythrocyte Removal Step In this example, it was demonstrated that culture with differentiation induction media, results in induction of differentiation into a variety of differentiated cells, even if the raw materials were prepared without erythrocyte removal step.

The differentiation steps used are the same as in Example 19.

Similar results are obtained as in Example 19. As a result, the stem cells as prepared without erythrocyte removal step, showed good quality of pluripotency.

Example 21: Quantification

The present Example demonstrates the stem cell number that can be obtained from material from liposuction. The quantification was conducted by simply counting cell number per certain volume of a cell sample.

The results are shown in the following table. The following table includes cell number just after the preparation and seven days after culturing for seven days. By culturing stem cell samples, blood cells are removed and the concentration of stem cell was observed to increase.

| | | | | | Just after preparation | | | | Seven days after culture | | | |
|---|---|---|---|---|---|---|---|---|---|---|---|---|
| days of storage | age | sex | fat volume (PLA) (ml) | fat volume (LAF) (ml) | cell number per 1000 ml pf PLA (including blood cells) | cell number per 1000 ml of LFA (including blood cells) | cell number per 100 mm-dish (including blood cells) for PLA seed | cell number per 100 mm-dish (including blood cells) for LFA seed | cell number per 1000 ml of PLA after seven days (no blood cells) | cell number per 1000 ml of LFA after seven days (no blood cells) | ratio | PLA + LAF |
| 0 | 41 | F | 83.3 | 83.3 | 1.32E+09 | 2.52E+09 | 6.00E+07 | 1.10E+08 | 5.28E+07 | 9.17E+06 | 5.76 | 6.20E+07 |
| 0 | 31 | F | 250 | 200 | 2.60E+08 | 1.00E+08 | 6.50E+07 | 1.00E+07 | 4.49E+07 | 2.59E+07 | 1.73 | 7.08E+07 |
| 1 | 26 | F | 500 | 400 | 2.40E+09 | 3.25E+08 | 6.00E+08 | 6.50E+07 | 3.52E+06 | 1.22E+07 | 0.27 | 1.55E+07 |
| 0 | | F | 1000 | 500 | 1.60E+09 | 1.96E+10 | 4.00E+08 | 2.45E+09 | 9.60E+06 | 1.76E+07 | 0.55 | 2.72E+07 |
| 0 | | F | 30 | 14 | 1.93E+08 | 3.50E+09 | 5.80E+07 | 4.90E+07 | 2.93E+07 | 9.29E+06 | 3.15 | 3.86E+07 |
| 1 | 30 | F | 500 | 1000 | 1.20E+09 | 4.40E+08 | 5.00E+07 | 1.50E+08 | 6.45E+06 | 2.01E+06 | 3.21 | 8.46E+06 |
| 0 | 29 | F | 1000 | 2200 | 2.60E+09 | 1.14E+08 | 5.00E+06 | 1.00E+06 | 4.26E+08 | 5.01E+07 | 8.50 | 4.76E+08 |
| 0 | 29 | F | 400 | 400 | 2.00E+09 | 2.00E+08 | 5.00E+06 | 1.00E+06 | 3.46E+07 | 3.98E+06 | 8.69 | 3.86E+07 |
| 0 | 40 | F | 500 | 500 | 5.20E+08 | 1.64E+08 | 5.00E+06 | 5.00E+06 | 4.65E+07 | 3.06E+07 | 1.52 | 7.71E+07 |
| 0 | | F | 800 | 500 | 1.16E+09 | 1.50E+08 | 5.00E+06 | 5.00E+06 | 7.10E+07 | 6.22E+07 | 1.14 | 1.33E+08 |
| 0 | | F | 500 | 625 | 7.84E+08 | 1.06E+08 | 5.00E+06 | 5.00E+06 | 5.60E+07 | 1.22E+07 | 4.59 | 6.82E+07 |
| 0 | | F | 75 | 75 | 5.87E+08 | 3.07E+07 | 5.00E+06 | 2.30E+06 | 4.66E+07 | 2.31E+07 | 2.02 | 6.97E+07 |
| 0 | 36 | F | 700 | 700 | 1.17E+08 | 6.75E+08 | 5.00E+06 | 1.00E+07 | 2.47E+07 | 3.56E+07 | 0.69 | 6.03E+07 |
| 0 | | F | 500 | 325 | 2.00E+08 | 1.48E+08 | 5.00E+06 | 5.00E+06 | 5.24E+07 | 9.87E+06 | 5.31 | 6.23E+07 |
| 0 | 29 | F | 250 | 50 | 1.76E+08 | 1.34E+09 | 5.00E+06 | 1.00E+07 | 4.19E+07 | 6.03E+06 | 6.95 | 4.79E+07 |
| 0 | 24 | F | 500 | 1000 | 1.34E+08 | 1.20E+08 | 5.00E+06 | 5.00E+06 | 6.78E+07 | 2.82E+07 | 2.40 | 9.60E+07 |
| 0 | 38 | F | 500 | 260 | 1.16E+08 | 1.88E+08 | 5.00E+06 | 5.00E+06 | 5.80E+07 | 5.17E+07 | 0.74 | 8.97E+07 |

| days of storage | age | sex | fat volume (PLA) (ml) | fat volume (LAF) (ml) | Just after preparation | | | | Seven days after culture | | ratio | PLA + LAF |
|---|---|---|---|---|---|---|---|---|---|---|---|---|
| | | | | | cell number per 1000 ml pf PLA (including blood cells) | cell number per 1000 ml of LFA (including blood cells) | cell number per 100 mm-dish (including blood cells) for PLA seed | cell number per 100 mm-dish (including blood cells) for LFA seed | cell number per 1000 ml of PLA after seven days (no blood cells) | cell number per 1000 ml of LFA after seven days (no blood cells) | | |
| 0 | 21 | F | 35 | 335 | 5.43E+08 | 6.29E+08 | 5.00E+06 | 5.00E+06 | 1.16E+07 | 4.19E+07 | 0.28 | 5.35E+07 |
| 0 | 27 | F | 500 | 95.6 | 3.92E+08 | 2.62E+09 | 2.00E+06 | 5.00E+06 | 2.16E+08 | 1.31E+08 | 1.65 | 3.47E+08 |
| 1 | 30 | F | 400 | 64.3 | 1.39E+08 | 8.29E+08 | 2.00E+06 | 5.00E+06 | 9.02E+07 | 1.96E+07 | 4.60 | 1.10E+08 |
| | | | | ave. | 9.09E+08 | 1.69E+09 | 6.49E+07 | 1.46E+08 | 6.85E+07 | 2.91E+07 | 2.35 | 9.76E+07 |
| | | | | S.D. | 8.17E+08 | 4.33E+09 | 1.54E+08 | 5.44E+08 | 9.55E+07 | 2.95E+07 | 3.24 | 1.13E+08 | ratio was calculated based on the following formula:

$$\text{Ratio} = \frac{\text{(cell number per 100 ml dish after seven days)}}{\text{(cell number per 100 ml dish before culture)}} \times \text{(cell number per 1000 ml before culture)}$$

As shown above, an aspirate from liposuction (LFA) contains comparable amount of stem cells to the solid fat tissue alone. Therefore, it is advantageous to use an aspirate from liposuction and/or material containing such an aspirate from liposuction and fat tissue as source for preparing stem cells.

Although certain preferred embodiments have been described herein, it is not intended that such embodiments be construed as limitations on the scope of the invention, except as set forth in the appended claims. All patents, published patent applications and publications cited herein are incorporated by reference as if set forth fully herein.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

INDUSTRIAL APPLICABILITY

The present invention confirmed that stem cells derived from an aspirate of liposuction which can be obtained in a simple manner, can be applied to regenerative medicine. Accordingly, those skilled in the art will readily find the industrial applicability of the present invention in pharmaceutical industries and the like.

What is claimed is:

1. A method for preparing a stem cell, without enzyme treatment, comprising:
   A) obtaining an aspirate from liposuction;
   B) subjecting the aspirate from liposuction to centrifugation to obtain a cell fraction;
   C) subjecting the cell fraction to centrifugation by specific gravity;
   D) collecting a cell layer with lower specific gravity than that of erythrocytes,
   E) resuspending the collected cell layer as a cell suspension and subjecting the cell suspension to centrifugation; and
   F) collecting the resulting cell pellet comprising the stem cell, wherein said method is absent any enzyme treatment step such that the method is carried out in a shorter time period in comparison to a method requiring enzyme treatment.

2. The method according to claim 1, wherein said aspirate from liposuction is prepared using saline or Ringer's solution.

3. The method according to claim 1, wherein said centrifugation is conducted at a speed of a range equal to or less than 800.times.g.

4. The method according to claim 1, wherein said centrifugation of step B) is conducted at a speed of a range equal to or less than 400.times.g.

5. The method according to claim 1, wherein said centrifugation by specific gravity is conducted at a speed of a range between 370.times.g and 1,100.times.g.

6. The method according to claim 1, wherein said centrifugation by specific gravity is conducted using medium which as a specific gravity of 1.076 to 1.078 g/ml at 20 degree Celsius.

7. The method according to claim 1, wherein the medium of said centrifugation by specific gravity is selected from the group consisting of Ficoll, Percoll and sucrose.

8. The method according to claim 7, wherein the medium of said centrifugation by specific gravity is Ficoll.

9. The method according to claim 1, wherein the specific gravity of the collected cell layer is at a range of between 1.050 and 1.075.

10. The method according to claim 1, wherein the collection of said cell layer is conducted using a pipette.

11. The method according to claim 1, further comprising the step of culturing the stem cell in a medium containing components selected from the group consisting of DMEM, M199, MEM, HBSS, Ham's F12, BME, RPM11640, MCDB104, MCDB 153 (KGM) and a mixture thereof.

12. The method according to claim 1, wherein the centrifugation by specific gravity comprises density gradient centrifugation.

13. The method according to claim 1, further comprising the step of removing blood cells.

14. A method for obtaining an explant, without enzyme treatment, comprising:
   A) obtaining an aspirate from liposuction;
   B) subjecting the aspirate from liposuction to centrifugation to obtain a cell fraction;
   E) subjecting the cell fraction to centrifugation by specific gravity;
   D) collecting a cell layer with lower specific gravity than that of erythrocytes;

E) resuspending the collected cell layer as a cell suspension and subjecting the cell suspension to centrifugation; and F) collecting the resulting cell pellet comprising stem cell, G) culturing the collected cell pellet comprising the stem cell to obtain an explant, wherein said method is absent any enzyme treatment step such that the method is carried out in a shorter time period in comparison to a method requiring enzyme treatment.

15. A method for preparing tissue transplant, without enzyme treatment, comprising:

A) obtaining an aspirate from liposuction;

B) subjecting the aspirate from liposuction to centrifugation to obtain a cell fraction;

C) subjecting the cell fraction to centrifugation by specific gravity;

D) collecting a cell layer with lower specific gravity than that of erythrocytes;

E) resuspending the collected cell layer as a cell suspension and subjecting the cell suspension to centrifugation; and F) collecting the resulting cell pellet comprising a stem cell, G) culturing the collected cell pellet comprising the stem cell to obtain a tissue transplant, wherein said method is absent any enzyme treatment step such that the method is carried out in a shorter time period in comparison to a method requiring enzyme treatment.

16. The method of claim 1, further comprising the step of filtering and removing any matrix component after the centrifugation of step B).

17. The method of claim 14, further comprising the step of filtering and removing any matrix component after the centrifugation of step B).

18. The method of claim 15, further comprising the step of filtering and removing any matrix component after the centrifugation of step B).

19. The method of claim 1, wherein said centrifugation of step B) is repeated.

20. The method of claim 14, wherein said centrifugation of step B) is repeated.

21. The method of claim 15, wherein said centrifugation of step B) is repeated.

* * * * *

UNITED STATES PATENT AND TRADEMARK OFFICE
CERTIFICATE OF CORRECTION

PATENT NO. : 9,631,176 B2  
APPLICATION NO. : 10/578213  
DATED : April 25, 2017  
INVENTOR(S) : Yoshimura et al.

Page 1 of 1

It is certified that error appears in the above-identified patent and that said Letters Patent is hereby corrected as shown below:

In the Claims

In Column 48, Line 64, please delete "E" and insert therefor --C--.

Signed and Sealed this  
Sixth Day of June, 2017

Michelle K. Lee  
*Director of the United States Patent and Trademark Office*